(12) United States Patent
Katsuki

(10) Patent No.: US 10,330,945 B2
(45) Date of Patent: Jun. 25, 2019

(54) MEDICAL IMAGE DISPLAY APPARATUS, MEDICAL INFORMATION PROCESSING SYSTEM, AND MEDICAL IMAGE DISPLAY CONTROL METHOD

(71) Applicant: Sony Olympus Medical Solutions Inc., Tokyo (JP)

(72) Inventor: Shinji Katsuki, Tokyo (JP)

(73) Assignee: Sony Olympus Medical Solutions Inc., Tokyo (JP)

( * ) Notice: Subject to any disclaimer, the term of this patent is extended or adjusted under 35 U.S.C. 154(b) by 0 days.

(21) Appl. No.: 15/897,173

(22) Filed: Feb. 15, 2018

(65) Prior Publication Data

US 2018/0259780 A1 Sep. 13, 2018

(30) Foreign Application Priority Data

Mar. 10, 2017 (JP) .................. 2017-046100

(51) Int. Cl.
| | | |
|---|---|---|
| *A61B 1/00* | (2006.01) | |
| *A61B 1/04* | (2006.01) | |
| *A61B 1/045* | (2006.01) | |
| *A61B 5/055* | (2006.01) | |
| *G02B 27/22* | (2018.01) | |
| *G06T 15/08* | (2011.01) | |
| *H04N 13/106* | (2018.01) | |

(Continued)

(52) U.S. Cl.
CPC ...... *G02B 27/2264* (2013.01); *A61B 1/00045* (2013.01); *A61B 1/045* (2013.01); *H04N 13/106* (2018.05); *H04N 13/341* (2018.05); *A61B 1/042* (2013.01); *A61B 5/055* (2013.01); *G06T 15/08* (2013.01); *H04N 13/282* (2018.05)

(58) Field of Classification Search
CPC ............... H04N 13/341; H04N 13/398; H04N 2213/008; H04N 13/356; H04N 13/359; H04N 13/286; H04N 13/289; H04N 13/332; H04N 13/167; G02B 27/2264; G02B 27/22; A61B 1/00193; G09G 3/003
See application file for complete search history.

(56) References Cited

U.S. PATENT DOCUMENTS

| | | | |
|---|---|---|---|
| 2011/0157318 A1* | 6/2011 | Nalibotski ......... | A61B 1/00193 348/65 |
| 2011/0234586 A1* | 9/2011 | Aoki .................. | H04N 13/0438 345/419 |
| 2013/0257860 A1* | 10/2013 | Tezuka .................... | G06T 15/00 345/419 |

FOREIGN PATENT DOCUMENTS

JP 5025769 9/2012

* cited by examiner

*Primary Examiner* — Haixia Du
(74) *Attorney, Agent, or Firm* — Oblon, McClelland, Maier & Neustadt, L.L.P.

(57) ABSTRACT

There is provided a medical image display apparatus including: a display control section that performs control such that a left-eye image and a right-eye image that form a medical image are displayed in a time division manner on a predetermined display section; and a communication section that transmits a synchronization signal in accordance with display timings of the left-eye image and the right-eye image on the display section to shutter glasses that include a left-eye shutter and a right-eye shutter, and receives a response to the synchronization signal from the shutter glasses. The display control section performs the control such that only any one of the left-eye image and the right-eye image is displayed on the display section in accordance with a reception status of the response.

10 Claims, 13 Drawing Sheets

(51) Int. Cl.
*H04N 13/282* (2018.01)
*H04N 13/341* (2018.01)

MEDICAL IMAGE DISPLAY APPARATUS, MEDICAL INFORMATION PROCESSING SYSTEM, AND MEDICAL IMAGE DISPLAY CONTROL METHOD

CROSS REFERENCE TO RELATED APPLICATIONS

This application claims the benefit of Japanese Priority Patent Application JP 2017-046100 filed Mar. 10, 2017, the entire contents of which are incorporated herein by reference.

BACKGROUND

The present disclosure relates to a medical image display device, a medical information processing system, and a medical image display control method.

Recently, due to advancements in surgical techniques and surgical equipment, surgeries for performing various treatments (also called microsurgery) while observing an affected site with an observation device for medical use, such as a surgical microscope or an endoscope, are coming to be conducted frequently. Also, such observation devices for medical use are not limited to devices that enable optical observation of the affected area, and also include devices that display an image of the affected area captured by an imaging section (camera) or the like as an electronic image on a display device such as a display.

In addition, when displaying, on a display device, an image of an affected area (hereinafter, also referred to as a "medical image") captured by an imaging section of an observation device, the image often is displayed as a flat two-dimensional (2D) image. However, since a sense of perspective is difficult to obtain from a 2D image, and the relative distance between the affected area and a treatment tool may be difficult to grasp, in recent years, technology that displays a captured image of an affected area as a stereoscopic three-dimensional (3D) image has also been developed.

In this way, in an observation device that displays a captured image of an affected area as a stereoscopic three-dimensional (3D) image (hereinafter designated a "stereoscopic observation device" in some cases), for example, by causing the left and right eyes to observe different viewpoint images, the user is made to observe an image of the affected area as a stereoscopic three-dimensional image. Note that a viewpoint image to be observed by a left eye will also be referred to as a "left-eye image," and a viewpoint image to be observed by a right eye will also be referred to as a "right-eye image" in the present disclosure.

In particular, a shutter glasses scheme has attracted attention as a scheme for realizing three-dimensional image observation in recent years as resolution of display devices has increased (high definition). The shutter glasses scheme is a scheme for realizing three-dimensional image observation by displaying a left-eye image and a right-eye image in a time division manner on a display device and causing the left-eye image and the right-eye image to be individually observed through shutter glasses.

SUMMARY

Incidentally, it is necessary to cause opening and closing of a right-eye shutter and a left-eye shutter of the shutter glasses to be synchronized with timings at which the left-eye image and the right-eye image are displayed on the display device in the case of employing the shutter glasses scheme. As a method for realizing such synchronization between the display device and the shutter glasses, a method of causing the shutter glasses to synchronize the opening and the closing of the right-eye shutter and the left-eye shutter on the basis of a synchronization signal transmitted from the display device is known. For example, Japanese Patent No. 5025769 discloses an example of a technique of controlling opening and closing each shutter of shutter glasses in accordance with a synchronization signal transmitted from a display device.

Meanwhile, if it becomes difficult to establish synchronization between the display device and the shutter glasses in the shutter glasses scheme, it becomes difficult to perform three-dimensional image observation, and there are also cases in which blur or the like of an outline occurs and it thus becomes difficult to perform observation itself of a target that is displayed as an image (for example, a medical image). In a medical setting in which the observation device for medical use as described above is used, in particular, occurrence of the circumstances in which it is difficult to observe the image of the affected site captured by the observation device for medical use is not preferable. Therefore, it is desirable to maintain a state in which observation of an image of an observation target (in other words, observation of an image of a display target) is available for as long as possible even under the circumstance in which it is difficult to perform three-dimensional image observation, in a setting in which higher reliability is requested, such as a medical setting.

Thus, the present disclosure proposes a medical image display apparatus, a medical information processing system, and a medical image display control method capable of allowing observation of a medical image that is a display target to continue even in a case in which it is difficult to establish synchronization between the display device and the shutter glasses.

According to an embodiment of the present disclosure, there is provided a medical image display apparatus including: a display control section that performs control such that a left-eye image and a right-eye image that form a medical image are displayed in a time division manner on a predetermined display section; and a communication section that transmits a synchronization signal in accordance with display timings of the left-eye image and the right-eye image on the display section to shutter glasses that include a left-eye shutter and a right-eye shutter, and receives a response to the synchronization signal from the shutter glasses. The display control section performs the control such that only any one of the left-eye image and the right-eye image is displayed on the display section in accordance with a reception status of the response.

In addition, according to an embodiment of the present disclosure, there is provided a medical information processing system including: a medical image display apparatus that controls display of a medical image on a predetermined display section; and shutter glasses that include a left-eye shutter and a right-eye shutter. The medical image display apparatus includes a display control section that performs the control such that a left-eye image and a right-eye image that form the medical image are displayed in a time division manner on the display section, and a communication section that transmits a synchronization signal in accordance with display timings of the left-eye image and the right-eye image on the display section to the shutter glasses, and receives a response to the synchronization signal from the shutter glasses. The shutter glasses include a shutter control section that controls closing and opening of each of the left-eye shutter and the right-eye shutter on a basis of the synchronization signal. The display control section performs the control such that only any one of the left-eye image and the right-eye image is displayed on the display section in accordance with a reception status of the response.

In addition, according to an embodiment of the present disclosure, there is provided a medical image display control method including, by a computer: performing control such that a left-eye image and a right-eye image that form a medical image are displayed in a time division manner on a predetermined display section; transmitting a synchronization signal in accordance with display timings of the left-eye image and the right-eye image on the display section to shutter glasses that include a left-eye shutter and a right-eye shutter, and receiving a response to the synchronization signal from the shutter glasses; and performing control such that only any one of the left-eye image and the right-eye image is displayed on the display section in accordance with a reception status of the response.

According to an embodiment of the present disclosure, the medical image display apparatus, the medical information processing system, and the medical image display method capable of causing observation of a medical image that is a display target to be continued even in a case in which it is difficult to establish synchronization between the display device and the shutter glasses as described above are provided.

Note that the effects described above are not necessarily limitative. With or in the place of the above effects, there may be achieved any one of the effects described in this specification or other effects that may be grasped from this specification.

DETAILED DESCRIPTION OF THE EMBODIMENT(S)

Figure 1:
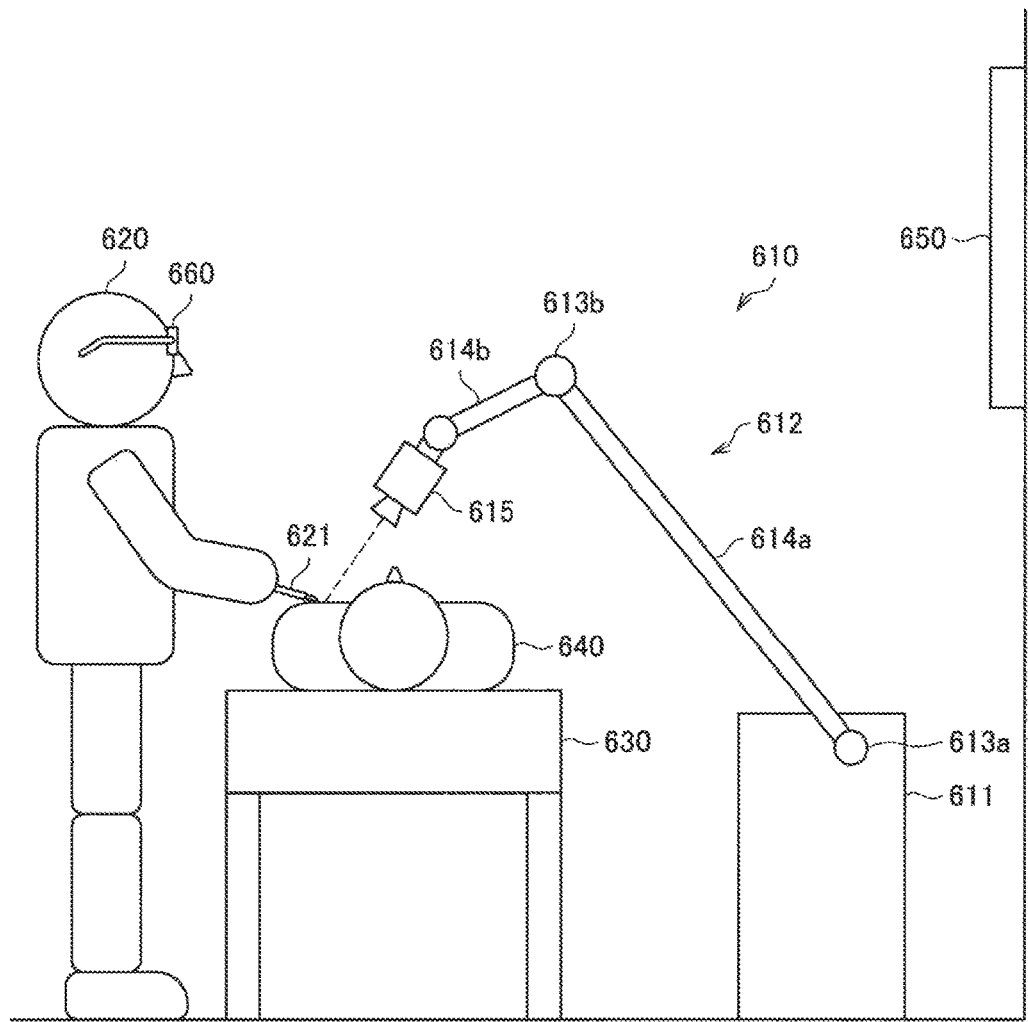
FIG. 1 is an explanatory diagram for explaining an example of an outline configuration of a medical stereoscopic observation device according to an embodiment of the present disclosure.

Hereinafter, (a) preferred embodiment(s) of the present disclosure will be described in detail with reference to the appended drawings. In this specification and the appended drawings, structural elements that have substantially the same function and structure are denoted with the same reference numerals, and repeated explanation of these structural elements is omitted.

In addition, description will be given in the following order.

1. Outline configuration of medical stereoscopic observation device
2. Discussion related to presentation of three-dimensional image
3. Technical features
3.1 Outline configuration
3.2 Functional configuration
3.3 Processing
3.4 Modification examples
4. Application example
4.1 First application example: hard endoscope device
4.2 Second application example: soft endoscope device
5. Hardware configuration
6. Conclusion <1. Outline Configuration Of Medical Stereoscopic Observation Device>

First, an example of an outline configuration of a medical stereoscopic observation device according to an embodiment of the present disclosure will be described to further clarify the present disclosure.

For example, FIG. 1 is an explanatory diagram for explaining an example of an outline configuration of a medical stereoscopic observation device according to an embodiment of the present disclosure. FIG. 1 illustrates an example in a case in which a surgical video microscope device that includes an arm is used as a medical stereoscopic observation device in an application example in a case in which the medical stereoscopic observation device according to the embodiment of the present disclosure is used.

For example, FIG. 1 diagrammatically illustrates how a medical procedure is performed using a surgical video microscope device according to the present embodiment. Specifically, referring to FIG. 1, a state is illustrated in which a physician acting as the surgeon (user) 620 is using a surgical tool 621, such as a scalpel, tweezers, or forceps, for example, to perform surgery on a subject (patient) 640 lying on an operating table 630. Note that in the following description, medical procedure is used as a collective term to denote various types of medical treatments performed by a physician acting as the user 620 on a patient acting as the subject 640, such as a surgery or an examination. Also, although the example illustrated in FIG. 1 illustrates a situation of surgery as an example of a medical procedure, the medical procedure in which the surgical video microscope device 610 is used is not limited to surgery, and may be any of various other types of medical procedures such as an examination using an endoscope.

Beside the operating table 630, the surgical video microscope device 610 according to the present embodiment is provided. The surgical video microscope device 610 is equipped with a base section 611 which acts as a base, an arm section 612 which extends from the base section 611, and an imaging unit 615 connected as a front edge unit on the front edge of the arm section 612. The arm section 612 includes multiple joint sections 613a, 613b, and 613c, multiple links 614a and 614b joined by the joint sections 613a and 613b, and the imaging unit 615 provided on the front edge of the arm section 612. In the example illustrated in FIG. 1, for the sake of simplicity, the arm section 612 includes three joint sections 613a to 613c and two links 614a and 614b, but in actuality, the degrees of freedom in the positions and the attitudes of the arm section 612 and the imaging unit 615 may be considered to appropriately configure factors such as the numbers and shapes of the joint sections 613a to 613c and the links 614a and 614b, and the directions of the drive shafts of the joints 613a to 613c, so as to achieve the desired degrees of freedom.

The joint sections 613a to 613c have a function of rotatably joining the links 614a and 614b to each other, and by driving the rotation of the joint sections 613a to 613c, the driving of the arm section 612 is controlled. Herein, in the following description, the position of each structural member of the surgical video microscope device 610 means the position (coordinates) in a space prescribed for drive control, while the attitude of each structural member means the direction (angle) with respect to an arbitrary axis in the space prescribed for drive control. Also, in the following description, the driving (or the drive control) of the arm section 612 refers to the driving (or the drive control) of the joint sections 613a to 613c, as well as to the position and attitude of each structural member of the arm section 612 being changed (or such change being controlled) by conducting the driving (or the drive control) of the joint sections 613a to 613c.

On the front edge of the arm section 612, the imaging unit 615 is connected as a front edge unit. The imaging unit 615 is a unit that acquires an image of an imaging target (that is, a medical image), and is a device such as a camera capable of capturing a moving image or a still image, for example. As illustrated in FIG. 1, the attitudes and the positions of the arm section 612 and the imaging unit 615 are controlled by the surgical video microscope device 610 so that the imaging unit 615 provided on the front edge of the arm section 612 captures the operating site of the subject 640. Note that the configuration of the imaging unit 615 connected as the front edge unit on the front edge of the arm section 612 is not particularly limited, and the imaging unit 615 may be configured as an endoscope or a microscope, for example. Additionally, the imaging unit 615 may also be configured to be removable from the arm section 612. According to such a configuration, an imaging unit 615 depending on the usage scenario may be connected appropriately to the front edge of the arm section 612 as the front edge unit, for example. Note that although the description herein focuses on a case in which the imaging unit 615 is applied as the front edge unit, obviously the front edge unit connected to the front edge of the arm section 612 is not necessarily limited to the imaging unit 615.

Also, at a position facing the user 620, a display device 650 such as a monitor or a display is installed. An image of the operating site captured by the imaging unit 615 is displayed as an electronic image on the display screen of the display device 650. The user 620 performs various treatments while looking at an electronic image of the operating site displayed on the display screen of the display device 650.

In this way, in the medical field, the present embodiment proposes performing surgery while imaging the operating site with the surgical video microscope device 610.

Particularly, the surgical video microscope device 610 according to an embodiment of the present disclosure (that is, a medical stereoscopic observation device) is configured to be able to acquire image data for displaying the imaging target as a three-dimensional image (3D image).

As a specific example, the surgical video microscope device 610 is provided with a stereo camera including two imaging section subsystems (for example, camera units) as the imaging unit 615, and thereby acquires, via each imaging section, images from multiple different viewpoints (in other words, viewpoint images).

Each of the multiple viewpoint images (that is, viewpoint images that form a medical image) acquired by the imaging unit 615 is subjected to various types of image processing by an image processing device built into or externally attached to the surgical video microscope device 610, and then displayed on the display device 650 as a left-eye image and a right-eye image (that is, a left-eye image and a right-eye image that form a medical image), respectively. Note that in this description, the right-eye image denotes a so-called parallax image having a set parallax for observing a viewpoint corresponding to the user's right eye, to enable the user to observe a 3D image. Similarly, the left-eye image denotes a parallax image having a set parallax for observing a viewpoint corresponding to the user's left eye, to enable the user to observe a 3D image.

Note that a variety of schemes have been proposed as mechanisms for allowing the user 620 to observe images displayed as the left-eye image and the right-eye image on the display device 650 as a three-dimensional image. As a specific example, a shutter glasses scheme in which left and right eyes are shown mutually different images (that is, the left-eye image and the right-eye image) in a time division manner by using dedicated glasses called shutter glasses is exemplified. In the example illustrated in FIG. 1, for example, the user 620 can observe a three-dimensional image of a site of a medical procedure by viewing electronic images of the site of the medical procedure, which are displayed on the display device 650, via shutter glasses 660.

In addition, the circumstances in which a medical observation device as described above is used also includes cases in which various information should be checked, including images of an affected area. Under such circumstances, usage patterns such as displaying images respectively on multiple displays or displaying multiple images inside a display may also be anticipated. As a specific example, a case is anticipated in which an overall picture of the affected area is displayed on one display, while a magnified image of the affected area is displayed on another display. As another example, a case is also anticipated in which an image of the affected area is displayed on one display, while an image captured by another imaging device, such as a computed tomography (CT) image or a magnetic resonance imaging (MRI) image, is displayed on another display. For this reason, multiple display devices 650 may also be provided in some cases.

The above thus references FIG. 1 to describe, as an applied example of using a medical stereoscopic observation device according to an embodiment of the present disclosure, a an example of a case in which a surgical video microscope device equipped with an arm is used as the medical stereoscopic observation device.

<2. Discussion Related To Presentation Of Three-Dimensional Image>

Next, influences of high definition of display on various schemes for realizing three-dimensional image observation will be described, and then problems addressed by a medical information processing system and a medical stereoscopic observation device according to an embodiment of the present disclosure will then be summarized.

First, an outline of an example of the schemes for realizing three-dimensional image observation will be described. As a scheme for realizing the three-dimensional image observation, a passive scheme and an active shutter scheme are exemplified, for example. The passive scheme and the active shutter scheme are schemes for allowing a user to observe a stereoscopic three-dimensional image by allowing the user to observe images that correspond to the left and right eyes (that is, a left-eye image and a right-eye image) while the passive scheme and the active shutter scheme have different mechanisms for allowing the user to observe the three-dimensional image, that is, different mechanisms for allowing the user to observe the images that correspond to the left and right eyes. Specifically, the passive scheme is a scheme in which both the right-eye image and the left-eye image are displayed in a screen of a display device, the right-eye image and the left-eye image are separated with a polarization filter, a color filter, or the like, and the user is allowed to observe the images that correspond to the left and right eyes. In addition, the shutter glasses scheme is a scheme in which the left-eye image and the right-eye image are displayed on the screen of the display device in the time division manner, and a left-eye shutter and a right-eye shutter provided in shutter glasses are made to open and close in synchronization with display timings of the respective images, thereby allowing the user to observe the images that correspond to the left and right eyes.

Figure 2:
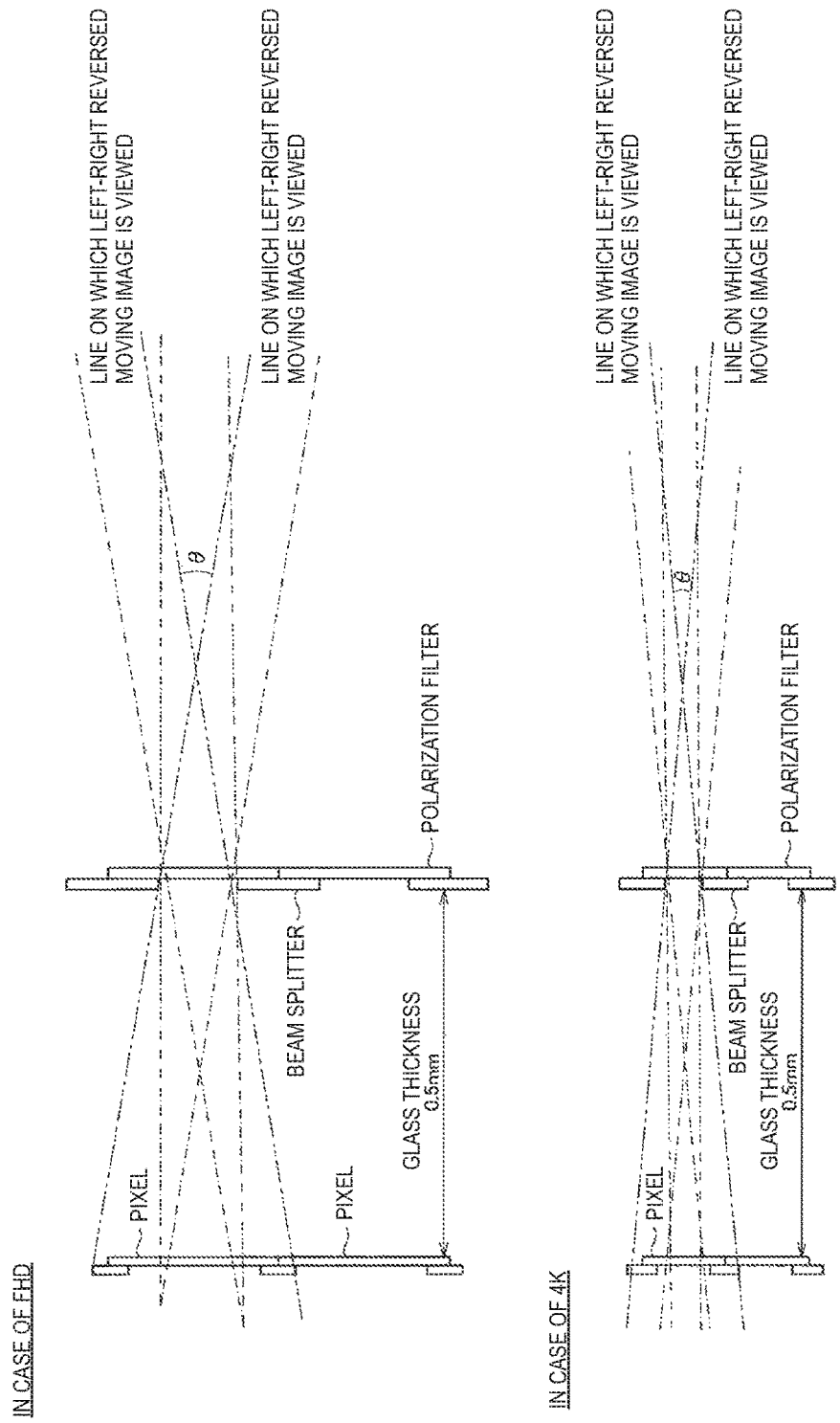
FIG. 2 is an explanatory diagram for explaining an influence of high definition of a display in a case in which a passive scheme is applied.

In a medical setting in which the medical stereoscopic observation device as described above is used, the passive scheme has mainly been used as a scheme for realizing the three-dimensional image observation in the related art. Meanwhile, it has become difficult to employ the passive scheme as resolution of display devices, such as displays, has increased in recent years. For example, FIG. 2 is an explanatory diagram for explaining an influence of an increase in resolution of a display in a case in which the passive scheme is applied, and illustrates an example of an outline structure for causing a three-dimensional image to be observed on the basis of the passive scheme. Specifically, FIG. 2 illustrates an example of an outline structure of a display panel in a case in which the display panel of the display device is cut along a plane that is perpendicular to both a horizontal plane and a display plane of the display panel and the cut surface is viewed from the side of a side surface of the display device. In addition, the up-down direction in FIG. 2 corresponds to the up-down direction (vertical direction) of the display panel of the display device while the depth direction in FIG. 2 corresponds to a left-right direction (horizontal direction) of the display panel. That is, the left-right direction in FIG. 2 corresponds to the front-back direction in a case in which the display panel is faced. In addition, the upper diagram in FIG. 2 illustrates an example of a case in which resolution is FHD (1920×1080 pixels). In addition, the lower diagram illustrates an example of a case in which resolution is 4K (3840×2160).

In a case in which the passive scheme is employed, the left-eye image and the right-eye image that are displayed on the display panel are separated by arranging optical members that have polarization properties, such as a pattern retarder, on a front surface of the display panel. In FIG. 2, for example, a beam splitter and a polarization filter correspond to the optical members, such as a pattern retarder, described above. Specifically, light from each pixel passes through the beam splitter positioned in front of the pixel and is then polarized by the polarization filter as illustrated in FIG. 2. In this manner, the light from the respective pixels is individually separated. Therefore, light from pixels that are used to display the left-eye image and light from pixels that are used to display the right-eye image can be separated, and the respective light can be shown to the corresponding eyes (that is, observation of the three-dimensional image can be enabled).

Meanwhile, in a case in which the passive scheme is employed, there are cases in which a phenomenon called crosstalk, in which images that are different from the images that correspond to the left and right eyes are observed (that is, the right eye-image is observed by the left eye, and the left-eye image is observed by the right eye) in accordance with a position of a viewer with respect to the display device (hereinafter, also referred to as a "viewing position"), occurs.

Specifically, in addition to light from a certain pixel, there is a case in which light from other pixels that are adjacent to the pixel leaks from the beam splitter that is positioned in front of the pixel as illustrated in FIG. 2. Therefore, there is a case in which images opposite to moving images to be observed by the left and right eyes are observed outside a vertical viewing angle represented by the reference numeral θ in FIG. 2, for example, and a moving image with blurred outlines or a moving image that leads to less sense of perspective is observed.

With such a configuration, the vertical viewing angle θ becomes narrower as a pixel pitch becomes narrower if the pixel pitch is changed without changing the glass thickness of the display panel, as can be understood from comparison between the respective cases of FHD and 4K illustrated in FIG. 2. Therefore, a case can be assumed in which it becomes substantially difficult to secure the vertical viewing angle θ without adjusting the glass thickness to be thinner if the increase in resolution (high definition) of the display panel further advances in the future. Also, conditions of precision necessary for attaching the optical members such as a pattern retarder to the display panel will become stricter as the resolution of the display panel increases. In addition, it is necessary to use a dedicated display device since it is necessary to attach the optical members such as a pattern retarder to the display panel in the case in which the passive scheme is employed.

Meanwhile, the shutter glasses scheme realizes three-dimensional image observation by causing the left-eye image and the right-eye image to be displayed in the time division manner as described above. With such properties, the shutter glasses scheme can realize display of the left-eye image and the right-eye image (and thus observation of the three-dimensional image) by software control without using the dedicated display device as in the passive scheme. In addition, since no crosstalk due to the configurations of the display panel and the optical members attached to the display panel as in the passive scheme can occur due to the aforementioned properties, it is not necessary to take restriction of the viewing angle θ described above as in the passive scheme into consideration. Because of such properties, the shutter glasses scheme has attracted attention as a scheme for realizing three-dimensional image observation as resolution of display devices has increased.

Incidentally, in a case in which the shutter glasses scheme is employed, it is necessary to synchronize opening and closing of the right-eye shutter and the left-eye shutter in the shutter glasses with timings at which the left-eye image and the right-eye image are displayed on the display device. As a method for realizing such synchronization between the display device and the shutter glasses, a method of causing the opening and the closing of the right-eye shutter and the left-eye shutter to be synchronized by the shutter glasses on the basis of a synchronization signal transmitted from the display device is known.

Meanwhile, there are cases in which it becomes difficult to observe the three-dimensional image if it becomes difficult to establish synchronization between the display device and the shutter glasses for some reason such as a difficulty in communication between the display device and the shutter glasses, for example, in the shutter glasses scheme. In a specific example, the phenomenon in which images different from the images that correspond to the left and right eyes are observed (that is, crosstalk), for example, can occur even in the shutter glasses scheme since the synchronization between the display device and the shutter glasses is not established. An event in which a moving image which leads to less sense of perspective, a moving image with blurred outlines, or the like is observed occurs, and it thus becomes difficult to perform proper observation itself of a target that is displayed as the image in some cases in such a situation in which it is difficult to establish the synchronization between the display device and the shutter glasses.

The event in which it becomes difficult to observe an image of an affected site captured by the observation device for medical use (that is, a medical image) is not preferable particularly in a medical setting in which the observation device for medical use described above with reference to FIG. 1 is used. Therefore, it is desirable that a state in which observation of an image of an observation target (in other words, a medical image of a display target) is possible be maintained for as long as possible even under the situation in which it is difficult to observe the three-dimensional image in settings that request higher reliability, such as a medical setting.

In view of such circumstances, the present disclosure proposes examples of techniques that enable continuous observation of a medical image that is a display target even in a case in which it is difficult to establish synchronization between the display device and the shutter glasses. Thus, the medical information processing system according to an embodiment of the present disclosure will be described below in detail while focusing on technical features thereof.
<3. Technical Features>

Next, an example of a system that presents an image of an affected site to a viewer such as a practitioner by using the aforementioned medical stereoscopic observation device will be described as a medical information processing system according to an embodiment of the present disclosure with particular focus on technical features of the system.
<3.1. Outline Configuration>

Figure 3:
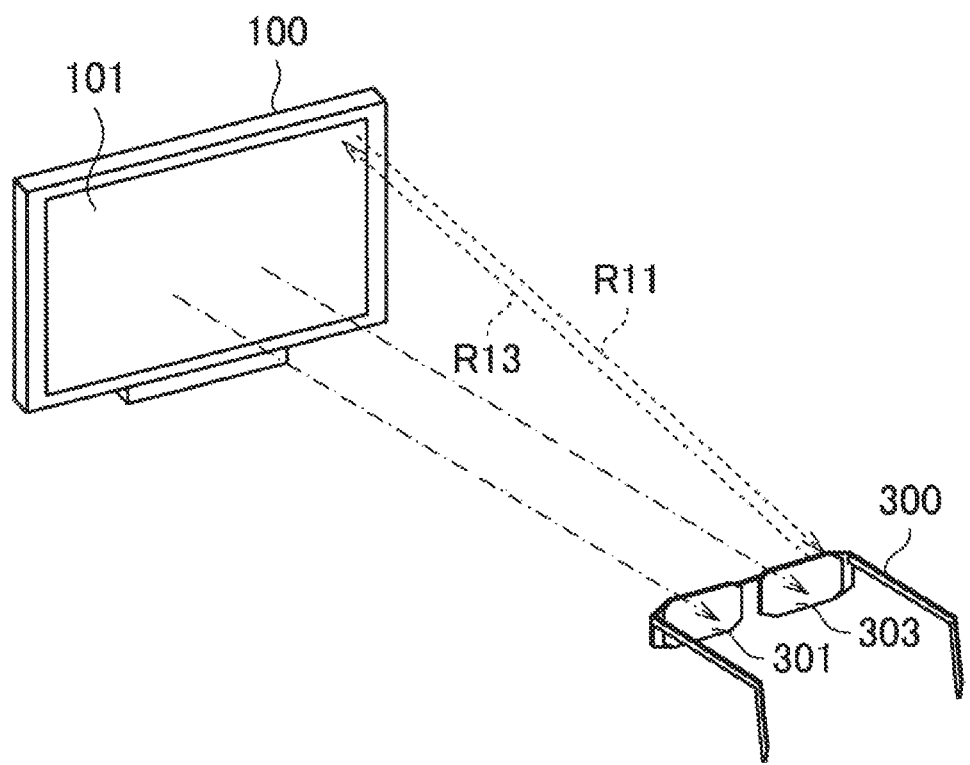
FIG. 3 is an explanatory diagram for explaining an example of a schematic system configuration of a medical information processing system according to the embodiment.

First, an example of an outline system configuration of the medical information processing system according to the embodiment will be described with reference to FIG. 3. FIG. 3 is an explanatory diagram for explaining an example of the outline system configuration of the medical information processing system according to the embodiment.

A medical information processing system 1 according to the embodiment includes, for example, a display device 100 and shutter glasses 300 and allows the viewer to observe a medical image (for example, an image of an affected site captured by an imaging device such as a surgical microscope, an endoscope, an operative field camera, or a surgery camera) that is a display target as a three-dimensional image on the basis of the shutter glasses scheme.

Specifically, the display device 100 displays a left-eye image and a right-eye image in accordance with an image that is a display target on a display section 101 (for example, a display panel) in the time division manner and transmits a synchronization signal R11 in accordance with the respective display timings of the left-eye image and the right-eye image to the shutter glasses 300.

The shutter glasses 300 include a left-eye shutter 301 that is held in front of a left eye of the viewer and a right-eye shutter 303 that is held in front of a right eye of the viewer in a case of being worn by the viewer. With such a configuration, the shutter glasses 300 control the respective opening and closing timings of the left-eye shutter 301 and the right-eye shutter 303 on the basis of the synchronization signal R11 transmitted from the display device 100. That is, the control is performed such that the left-eye shutter 301 opens in synchronization with a timing at which the left-eye image is displayed on the display section 101 of the display device 100 and the right-eye shutter opens in synchronization with a timing at which the right-eye image is displayed on the display section 101. It is possible to allow the corresponding eyes to observe the left-eye image and the right-eye image in this manner, and to thereby allow the viewer to observe the medical image that is a display target as a three-dimensional image.

In addition, the shutter glasses 300 receives the synchronization signal R11 from the display device 100 and then transmits a response signal R13 as a response to the synchronization signal R11 to the display device 100 in accordance with a result of the reception, in the medical information processing system 1 according to the embodiment. For example, the shutter glasses 300 provide, in the response signal R13, a notification indicating whether or not the synchronization signal R1 transmitted from the display device 100 has been properly received, to the display device 100.

The display device 100 recognizes whether or not the synchronization signal R11 has been properly received by the shutter glasses 300 on the basis of the response signal R13 transmitted from the shutter glasses 30 as a response to the synchronization signal R11. In a specific example, the display device 100 recognizes whether or not the shutter glasses 30 have been able to properly receive the synchronization signal R11 on the basis of the content of the response (for example, whether or not the synchronization signal R11 has been able to be properly received) of the notification provided in the response signal R13 from the shutter glasses 300. In addition, in a case in which the display device 100 fails to receive the response signal R13 in a predetermined period of time after the display device 100 transmits the synchronization signal R11 to the shutter glasses 300, the display device 100 may recognize that the shutter glasses 300 have not been able to properly receive the synchronization signal R11.

With such a configuration, the display device 100 selectively switches presentation of a three-dimensional image and presentation of a two-dimensional image in accordance with a reception status of the response signal R13 from the shutter glasses 300 in the medical information processing system 1 according to the embodiment.

In a specific example, the display device 100 continues the presentation of the three-dimensional image (that is, time-division display of the left-eye image and the right-eye image) as long as the display device 100 recognizes that the shutter glasses 300 have been able to properly receive the synchronization signal R11 in accordance with the reception status of the response signal R13.

Meanwhile, the display device 100 switches the presentation of the three-dimensional image to the presentation of the two-dimensional image in a case in which the display device 100 recognizes that the shutter glasses 300 have not been able to properly receive the synchronization signal R11 in accordance with the reception status of the response signal R13. In this case, the display device 100 performs control such that only one of the left-eye image and the right-eye image is displayed on the display section 101. In this manner, only one of the images is observed by each of the left and right eyes of the viewer regardless of an operation status of the shutter glasses, that is, the image displayed on the display section 101 is observed as a two-dimensional image by the viewer.

In addition, the display device 100 may switch the display to the presentation of the two-dimensional image and then switch the display again to the presentation of the three-dimensional image in a case in which the display device 100 recognizes that the shutter glasses 300 can properly receive the synchronization signal R11 in accordance with the reception status of the response signal R13.

With the configuration as described above, the display device 100 can switch a presentation mode of an image in accordance with input image data to a mode related to the presentation of the two-dimensional image in a case in which it becomes difficult to establish synchronization with the shutter glasses 300 (that is, in a case in which it becomes difficult to observe the three-dimensional image). In this manner, even in the case in which it is difficult to observe the three-dimensional image, it is possible to maintain the state in which the observation of the target displayed as an image (in other words, observation of an image that is a display target) can be performed (that is, to allow the viewer to continue the observation) while it is difficult to observe an image with a sense of perspective.

The example of the outline system configuration of the medical information processing system according to the embodiment has been described above with reference to FIG. 3.

<3.2 Functional Configuration>

Figure 4:
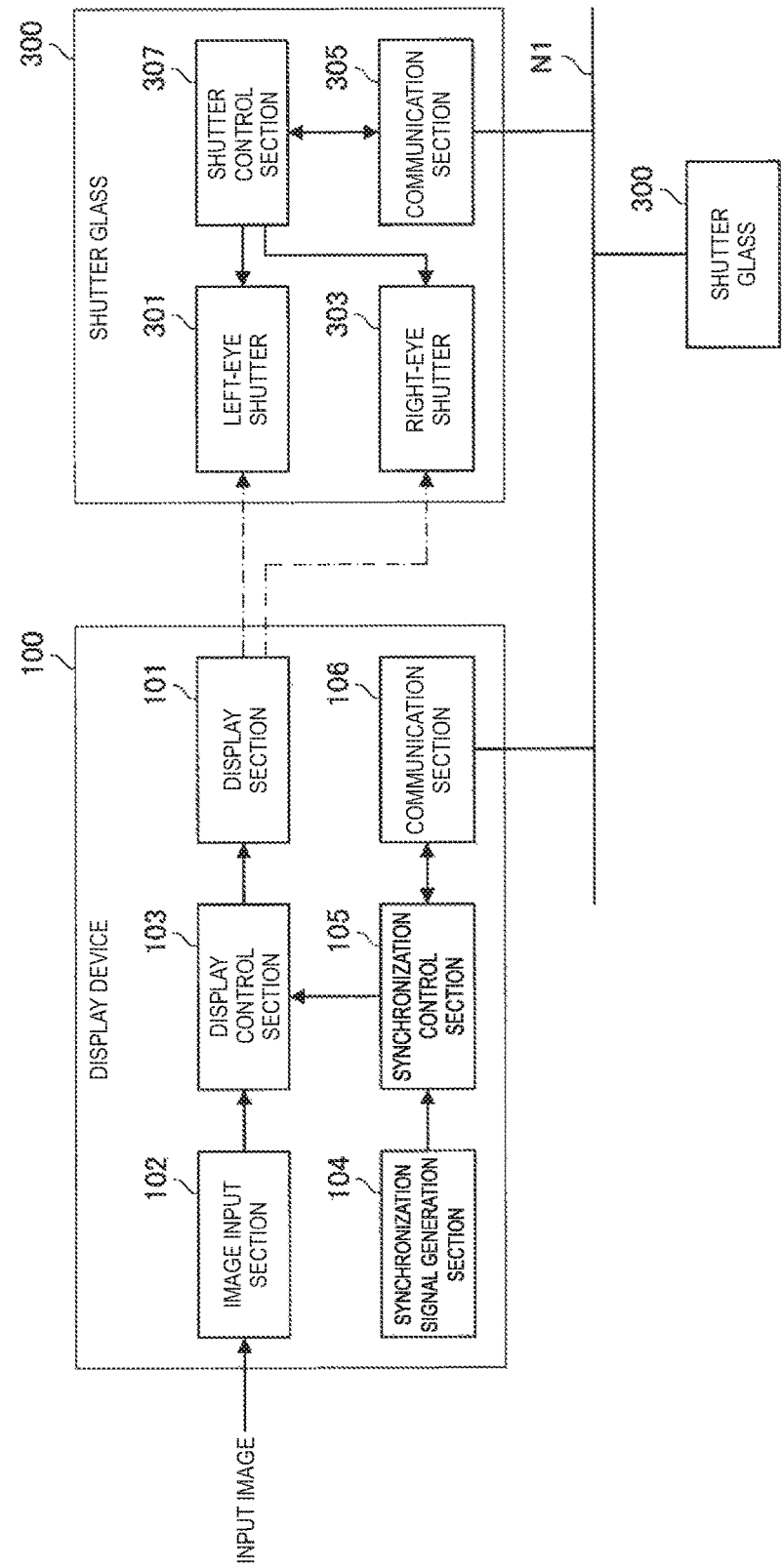
FIG. 4 is a block diagram illustrating an example of a functional configuration of the medical information processing system according to the embodiment.

Next, an example of a functional configuration of the medical information processing system 1 according to the embodiment will be described with reference to FIG. 4. FIG. 4 is a block diagram illustrating an example of a functional configuration of the medical information processing system 1 according to the embodiment.

The display device 100 and the shutter glasses 300 in FIG. 4 correspond to the display device 100 and the shutter glasses 300 illustrated in FIG. 3. In addition, the display device 100 and the shutter glasses 300 are configured to be able to mutually transmit and receive information via a network N1 in the example illustrated in FIG. 4. In addition, the medical information processing system 1 may include a plurality of shutter glasses. In this case, the display device 100 mutually transmits and receives information to and from each of the plurality of shutter glasses 300 via the network N1.

(Display Device 100)

Next, a configuration of the display device 100 will be described. As illustrated in FIG. 4, the display device 100 includes the display section 101, an image input section 102, a display control section 103 a synchronization signal generation section 104, a synchronization control section 105, and a communication section 106.

The display section 101 corresponds to the display panel of the display device 100. An image that is a display target is displayed on the display section 101 on the basis of control performed by the display control section 103, which will be described later.

The image input section 1-2 corresponds to an input interface for inputting image data of the image that is a display target. For example, image data based on a result of capturing an image by an imaging device, such as a surgical microscope, an endoscope, an operative field camera, or a surgery camera is input to the display device 100 via the image input section 102. In addition, the image data input via the image input section 102 will also be referred to as "input image data" below.

The communication section 106 is a communication interface for the display device 100 to transmit and receive various kinds of information to and from the shutter glasses 300 via the predetermined network N1. Note that the configuration of the communication section 106 may appropriately be changed in accordance with a communication scheme with the shutter glasses 300. In a case in which the display device 100 and the shutter glasses 300 perform communication via a wireless communication path, for example, the communication section 106 may include a base band processor, a radio frequency (RF) circuit, or the like. Note that transmission and reception of information are assumed to be performed via the communication section 106 unless otherwise particularly described, in a case in which a configuration in the display device 100 transmits and receives information to and from another device (for example, the shutter glasses 300) in the following description.

The synchronization signal generation section 104 generates a synchronization signal for displaying the left-eye image and the right-eye image in accordance with the input image data in the time division manner (that is, the synchronization signal in accordance with the respective display timings of the left-eye image and the right-eye image). The synchronization signal generation section 104 outputs the generated synchronization signal to the synchronization control section 105.

The display control section 103 causes the display section 101 to display an image in accordance with the input image data that is input via the image input section 102, thereby presenting the image to the viewer. Note that at this time, the display control section 103 may selectively switch a mode related to the presentation of the image between a mode related to presentation of a three-dimensional image and a mode related to presentation of a two-dimensional image on the basis of control performed by the synchronization control section 105, which will be described later.

Specifically, the display control section 103 causes the display section 101 to display a left-eye image and a right-eye image in accordance with the input image data in the time division manner on the basis of the synchronization signal supplied from the synchronization control section 105 in a case of presenting the three-dimensional image to the viewer. In addition, the display control section 103 causes the display section 101 to display only any one of the left-eye image and the right-eye image in accordance with the input image data, for example, in a case of presenting the two-dimensional image to the viewer.

Note that a generation source of the left-eye image and the right-eye image is not particularly limited. In a specific example, the left-eye image and the right-eye image may be generated by an imaging device provided with a plurality of imaging sections, such as a so-called stereo camera, on the basis of a result of capturing images from a plurality of points of view. In this case, the left-eye image and the right-eye image are input as the input image data to the display device 100. In addition, image data in accordance with a result of capturing an image by an imaging device such as a so-called monocular camera may be input as the input image data to the display device 100 in another example. In this case, the display control section 103 may generate the left-eye image and the right-eye image on the basis of the input image data. In addition, the display control section 103 may generate the left-eye image and the right-eye image on the basis of the image data corresponding to an image captured by a distance measurement sensor or the like by using a result of measuring the distance to an object captured in the image at this time.

The synchronization control section 105 supplies the synchronization signal output from the synchronization signal generation section 104 to the display control section 103 and also transmits the synchronization signal to the shutter glasses 300 via the network N1. In addition, the synchronization control section 105 attempts to receive a response signal transmitted from the shutter glasses 300 as a response to the synchronization signal. Then, the synchronization control section 105 recognizes whether or not the synchronization signal has been properly received by the shutter glasses 300 in accordance with a reception status of the response signal and controls operations related to the presentation of the image by the display control section 103 in accordance with the result of the recognition.

Specifically, the synchronization control section 105 causes the display control section 103 to continue the presentation of the three-dimensional image as long as the synchronization control section 105 recognizes that the shutter glasses 300 have been able to properly receive the synchronization signal. In this case, the display control section 103 displays the left-eye image and the right-eye image in the time division manner on the basis of the synchronization signal supplied from the synchronization control section 105.

Meanwhile, the synchronization control section 105 provides an instruction for presenting the two-dimensional image to the display control section 103 in a case in which the synchronization control section 105 recognizes that the shutter glasses 300 have not been able to properly receive the synchronization signal. In this case, the display control section 103 causes the display section 101 to display only any one of the left-eye image and the right-eye image.

In addition, the synchronization control section 105 may provide an instruction for presenting the three-dimensional image to the display control section 103 in a case in which the synchronization control section 105 recognizes that the shutter glasses 300 have been able to properly receive the synchronization signal after the synchronization control section provides the instruction for presenting the two-dimensional image to the display control section 103.

(Shutter Glasses 300)

Next, a configuration of the shutter glasses 300 will be described. As illustrated in FIG. 4, the shutter glasses 300 include the left-eye shutter 301 and the right-eye shutter 303, a communication section 305, and a shutter control section 307. Note that detailed description will be omitted for the left eye-shutter 301 and the right-eye shutter 303 since the description thereof has been given above with reference to FIG. 3.

The communication section 305 is a communication interface for the shutter glasses 300 to transmit and receive various kinds of information to and from the display device 100 via the predetermined network N1. Note that the configuration of the communication section 305 may be appropriately changed in accordance with the communication scheme with the display device 100 in the same manner as the aforementioned communication section 106. Note that the transmission and the reception of the information are assumed to be performed via the communication section 305 unless otherwise particularly described in a case in which a configuration in the shutter glasses 300 transmits and receives information to and from another device (for example, the display device 100) in the following description.

The shutter control section 307 controls the opening and the closing of each of the left eye shutter 301 and the right eye shutter 303 to synchronize with the timing indicated by the synchronization signal on the basis of the synchronization signal transmitted from the display device 100 via the network N1.

In addition, the shutter control section 307 transmits the response signal as a response to the synchronization signal to the display device 100 via the network N1 in accordance with the reception status of the synchronization signal transmitted from the display device 100. For example, the shutter control section 307 provides a notification indicating whether or not the synchronization signal has been able to be properly received by the response signal to the display device 100.

Note that the aforementioned configuration of the medical information processing system 1 is just an example and is not necessarily limited to the example illustrated in FIG. 4. In a specific example, a part of the respective configurations in the display device 100 may be provided outside the display device 100. In a more specific example, portions related to synchronization control and display control (for example, the synchronization signal generation section 104, the synchronization control section 105, the communication section 106, the display control section 103, and the like) from among the respective configurations in the display device 100 may be configured as other devices that are externally provided outside the display device 100. Note that other devices externally provided outside the display device 100 correspond to examples of the medical image display apparatus".

The example of the functional configuration of the medical information processing system according to the embodiment has been described above with reference to FIG. 4.

<3.3. Processing>

Next, an example of a flow of a series of processing performed by the medical information processing system 1 according to the embodiment will be described with reference to FIGS. 5 to 7 while focusing on operations of the display device 100, in particular. For example, FIG. 5 is a flowchart illustrating an example of a flow of a series of processing performed by the medical information processing system 1 according to the embodiment.

Figure 5:
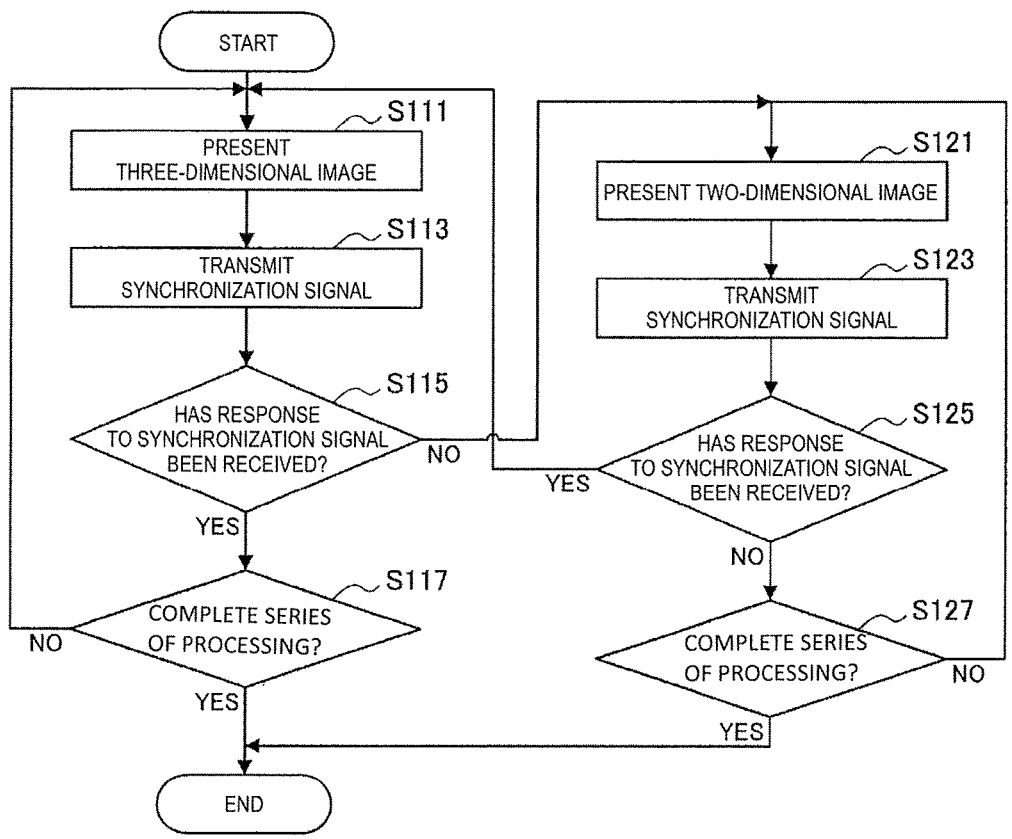
FIG. 5 is a flowchart illustrating an example of a flow of a series of processing performed by the medical information processing system according to the embodiment.

First, the display device 100 (display control section 103) presents a three-dimensional image to the viewer on the basis of the input image data input via the image input section 102 as illustrated in FIG. 5. Specifically, the display device 100 causes the display panel (display section 101) to display the left-eye image and the right-eye image in accordance with the input image data in the time division manner on the basis of the generated synchronization signal (S111).

In addition, the display device 100 (synchronization control section 105) transmits the generated synchronization signal to the shutter glasses 300 via the predetermined network N1 (S113). Then, the synchronization control section 105 attempts to receive the response signal transmitted from the shutter glass 300 as a response to the synchronization signal and selectively switches the following operations related to the display of the image in accordance with the input image data in accordance with the reception status of the response signal.

For example, the display device 100 (synchronization control section 105) recognizes that the shutter glasses 300 have been able to properly receive the synchronization signal in a case in which the response signal has been able to be properly received from the shutter glasses 300 (YES in S115) as a response to the synchronization signal. In this case, the display device 100 (display control section 103) continues to present the three-dimensional image as long as there is no instruction for completing the series of processing (NO in S117).

Here, an example of a timing of each of operations of the display device 100 and the shutter glasses 300 will be described in a case of presenting the three-dimensional image to the viewer, with reference to FIG. 6. FIG. 6 is an example of a timing chart related to presentation of an image in the medical information processing system 1 according to the embodiment and diagrammatically illustrates a timing of each of the operations of the display device 100 and the shutter glasses 300 in a case of presenting the three-dimensional image to the viewer. Specifically, the timing chart illustrated in FIG. 6 illustrates timings at which the display device 100 displays the left-eye image and the right-eye image and timings at which the shutter glasses 300 opens and closes each of the left-eye shutter and the right-eye shutter. Note that each of the left-eye image and the right-eye image is displayed on the display panel (display section 101) in an ON state and is not displayed on an OFF state in the example illustrated in FIG. 6. In addition, control is performed such that each of the left-eye shutter and the right-eye shutter opens in the ON state and closes in the OFF state.

Figure 6:
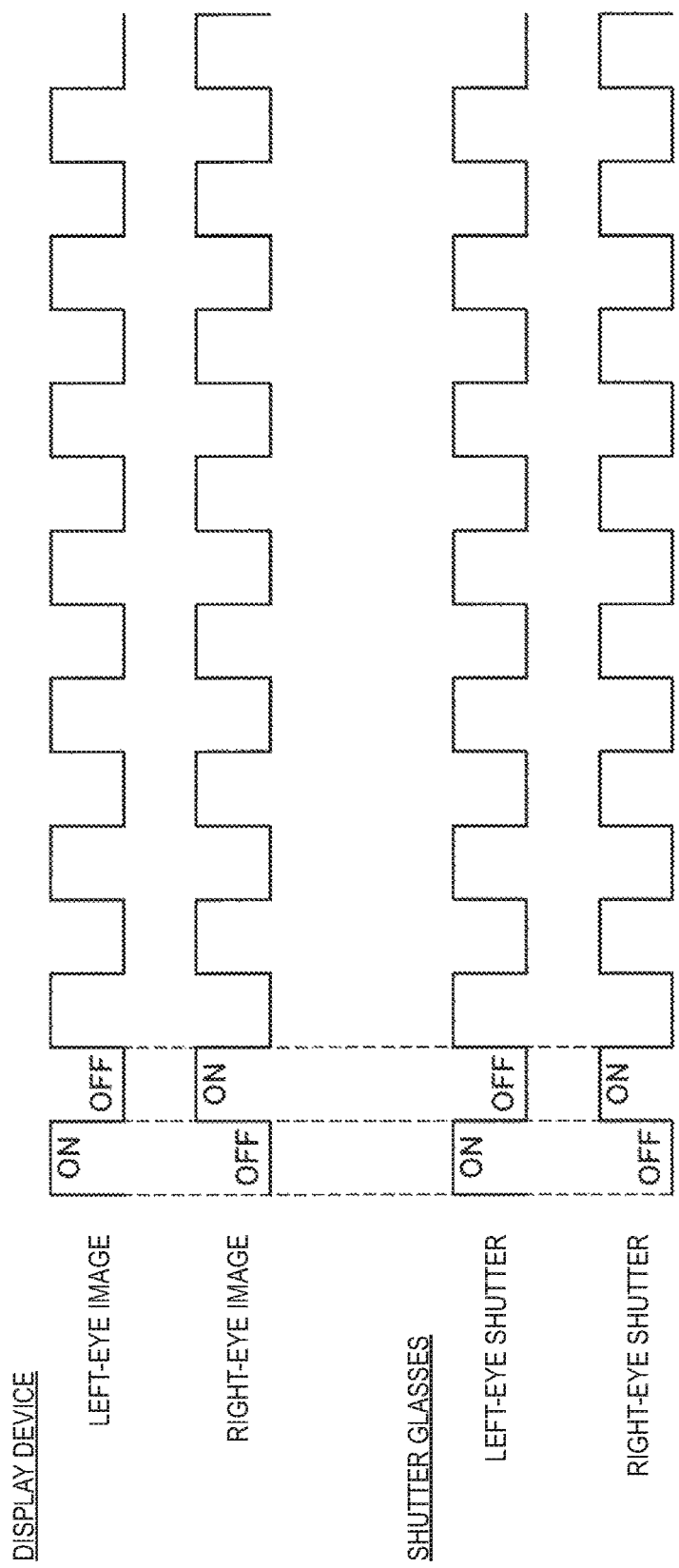
FIG. 6 illustrates an example of a timing chart related to presentation of an image by the medical information processing system according to the embodiment.

Specifically, the control is performed such that the left-eye shutter is opened and right-eye shutter is closed in synchronization with a timing at which the left-eye image is displayed at the timing, for example, in the example illustrated in FIG. 6. That is, the left-eye image is observed only by the left eye in the left and eye eyes of the viewer at the timing. In addition, the control is performed such that the left-eye shutter is closed and the right-eye shutter is opened in synchronization with a timing at which the right-eye image is displayed at the timing. That is, the right-eye image is observed only by the right eye in the left and right eyes of the viewer at the timing. The viewer observes the image that is a display target as a three-dimensional image by the control as described above.

Meanwhile, the display device 100 (synchronization control section 105) recognizes that the shutter glasses 300 have not been able to properly receive the synchronization signal in a case in which the response signal has not been able to be properly received from the shutter glasses 300 (S115, 300) as a response to the synchronization signal as illustrated in FIG. 5. In this case, the display device 100 (display control section 103) presents a two-dimensional image to the viewer on the basis of the input image data input via the image input section 102. Specifically, the display device 100 causes the display panel (display section 101) to display only any one of the left-eye image and the right-eye image in accordance with the input image data (S121).

In addition, the display device 100 (synchronization control section 105) transmits the generated synchronization signal to the shutter glasses 300 via the predetermined network N1 (S123) and attempts to receive the response signal transmitted from the shutter glasses 300 as a response to the synchronization signal.

The display device 100 (display control section 103) continues to present the two-dimensional image (S121) as long as there is no instruction for completing the series of processing (NO in S127) in a case where a situation in which the response signal has not been able to be properly received from the shutter glasses 300 continues (NO in S125).

Here, an example of a timing of each of operations of the display device 100 and the shutter glasses 300 in a case of presenting the two-dimensional image to the viewer will be described with reference to FIG. 7. FIG. 7 is an example of a timing chart related to presentation of an image by the medical information processing system 1 according to the embodiment and diagrammatically illustrates a timing of each of operations of the display device 100 and the shutter glasses 300 in a case of presenting the two-dimensional image to the viewer. Specifically, the timing chart illustrated in FIG. 7 illustrates timings at which the display device 100 displays the left-eye image and the right-eye image and timings at which the shutter glasses 300 opens and closes each of the left-eye shutter and the right-eye shutter in the same manner as in the example illustrated in FIG. 6. Note that the ON state and the OFF state of the left-eye image and the right-eye image and the ON state and the OFF state of the left-eye shutter and the right-eye shutter in the example illustrated in FIG. 7 are the same as those in the example illustrated in FIG. 6, In the example illustrated in FIG. 7, for example, the display device 100 switches the presentation of the three-dimensional image to the presentation of the two-dimensional image at the timing represented by the reference numeral t11. That is, the display device 100 performs control such that only the left-eye image in the left-eye image and the right-eye image is displayed on the display panel (display section 101) at and after the timing tn. In this case, the left-eye image is displayed on the display panel at any timing at which each of the left-eye shutter and the right-eye shutter is individually opened. That is, the left-eye image is observed by both the left and right eyes of the viewer. Therefore, the viewer observes the image that is a display target as a two-dimensional image by the control as described above.

Meanwhile, the display device 100 (synchronization control section 105) recognizes that the shutter glasses 300 have been able to properly receive the synchronization signal R11 in a case in which the display device 100 switches the display to the presentation of the two-dimensional image and then is able to properly receive the response signal from the shutter glasses 300 (YES in S125), as illustrated in FIG. 5. In this case, the display device 100 (display control section 103) switches the following operations related to the display of the image in accordance with the input image data from the operations related to the presentation of the two-dimensional image to the operations related to the presentation of the three-dimensional image (S111).

Then, the display device 100 completes the aforementioned series of processing related to the display of the image in accordance with the input image data if the instruction for completing the series of processing is provided (YES in S117 or YES in S127) such as shutting-down of a power source or stop of functions.

Figure 7:
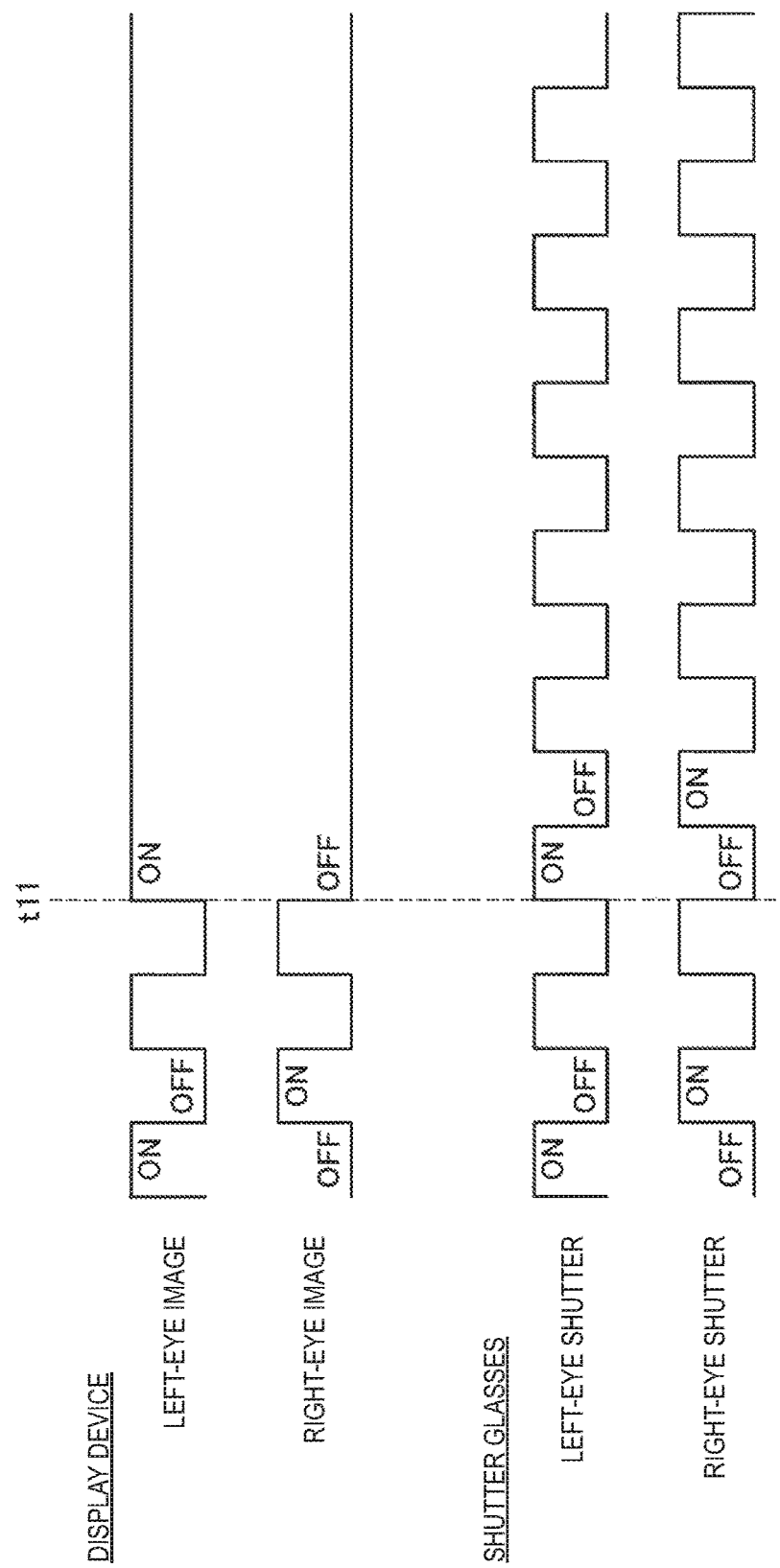
FIG. 7 illustrates an example of a timing chart related to presentation of an image by the medical information processing system according to the embodiment.

The example of the flow of the series of processing performed by the medical information processing system 1 according to the embodiment has been described above while focusing on the operations of the display device 100, in particular, with reference to FIGS. 5 to 7.

<3.4. Modification Examples>

Next, modification examples of the medical information processing system according to the embodiment will be described.

(Modification Example 1: Control Example in Case in Which Plurality of Shutter Glasses Operate)

First, an example of operations related to display of an image in accordance with a reception status of a response signal from each of the plurality of shutter glasses 300 in a case in which the display device 100 transmits a synchronization signal to the plurality of shutter glasses 300 will be described as Modification Example 1.

Figure 8:
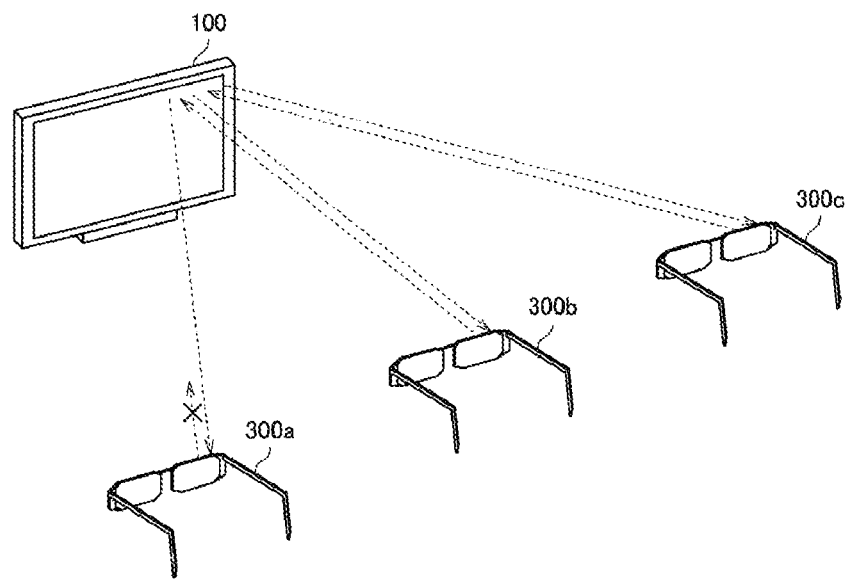
FIG. 8 is an explanatory diagram for explaining an aspect of operations performed by a medical information processing system according to Modification Example 1.

Under a situation in which the display device 100 attempts to receive the response signal transmitted from each of the plurality of shutter glasses 300 that have transmitted the synchronization signals, a case in which the response signals have not been able to be properly received from a part of the shutter glasses 300 can be assumed. For example, FIG. 8 is an explanatory diagram for explaining an aspect of operations of the medical information processing system according to Modification Example 1. Specifically, FIG. 8 illustrates an example in a case in which the display device 100 transmits synchronization signals to the respective shutter glasses 300a to 300c and receives response signals only from the shutter glasses 300b and 300c. That is, the display device 100 fails to properly receive the response signal from the shutter glasses 300a and recognizes that the shutter glasses 300a has not been able to properly receive the synchronization signal for some reason in the example illustrated in FIG. 8.

In this case, the display device 100 may control the operations related to the display of the image in accordance with the input image data depending on a viewer who uses the shutter glasses 300a that has not been able to properly receive the response signal (in other words, the user associated with the shutter glasses 300a), for example. In other words, the display device 100 may control the operations related to the display of the image in accordance with the input image data depending on the reception status of the response signal from the shutter glasses 300 (for example, the shutter glasses 300a) that a predetermined viewer uses from among the plurality of shutter glasses 300a to 300c.

In a specific example, it is assumed that a practitioner who performs various techniques while checking a result of imaging an affected site by the aforementioned observation device for medical use uses the shutter glasses 300a while an assistant, an anesthesiologist, a nurse, or the like uses the shutter glasses 300b or 300c. Under such a situation, it is assumed that the practitioner is set as the predetermined viewer described above from among the practitioner, the assistant, the anesthesiologist, and the nurse, for example. In this case, the display device 100 may switch the presentation mode of the image in accordance with the input image data from the mode related to the presentation of the three-dimensional image to the mode related to the presentation of the two-dimensional image in a case in which the display device 100 has not been able to properly receive the response signal from the shutter glasses 300a that the practitioner uses.

By such control, the image of the affected site is presented as a two-dimensional image to the practitioner even in a case in which it is difficult to establish synchronization between the display device 100 and the shutter glasses 300a and it is difficult for the practitioner that uses the shutter glasses 300a to observe the three-dimensional image of the affected site. Therefore, the practitioner can continue to observe the image of the affected site while it is difficult to observe the image of the affected site as a three-dimensional image that leads to a sense of perspective. Note that the shutter glasses 300 that the predetermined viewer uses (that is, the predetermined shutter glasses 300) may be set in advance as a monitoring target, for example. In addition, it is only necessary for the display device 100 to recognize the shutter glasses 300 as a transmission source of the response signal on the basis of information (for example, identification information or the like) associated with the response signal, for example. In this manner, the display device 100 can recognize the shutter glasses 300 even in a case in which the response signal from a part of shutter glasses 300 have not been able to be properly received.

Figure 9:
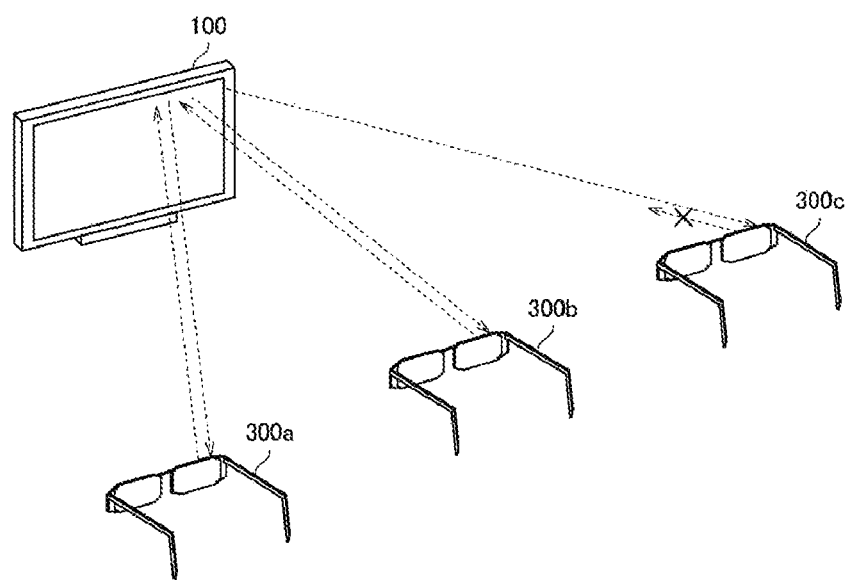
FIG. 9 is an explanatory diagram for explaining another aspect of operations performed by the medical information processing system according to Modification Example 1.

Meanwhile, FIG. 9 is an explanatory diagram for explaining another aspect of operations of the medical information processing system according to Modification Example 1. Specifically, FIG. 9 illustrates an example of a case in which the display device 100 transmits synchronization signals to the respective shutter glasses 300a to 300c and receives response signals only from the shutter glasses 300a and 300b. That is, the display device 100 fails to properly receive the response signal from the shutter glasses 300c and recognizes that the shutter glasses 300c fails to properly receive the synchronization signal for some reason in the example illustrated in FIG. 9.

Here, it is assumed that the practitioner who performs predetermined techniques is set as the predetermined viewer, that the practitioner uses the shutter glasses 300a, and that viewers other than the practitioner use the shutter glasses 300b and 300c in the similar manner to the example described above with reference to FIG. 8. That is, the example illustrated in FIG. 9 illustrates an example of a case in which it is difficult to establish synchronization between the display device 100 and the shutter glasses 300c and it is difficult for the viewers other than the practitioner who uses the shutter glasses 300c to observe a three-dimensional image of an affected site. In addition, the synchronization between the display device 100 and the shutter glasses 300a is established normally, and the practitioner who uses the shutter glasses 300a can properly observe the three-dimensional image of the affected site in the example illustrated in FIG. 9. In this case, the display device 100 may continue to present the three-dimensional image in accordance with the input image data.

Note that the aforementioned control of switching the presentation mode of the image in accordance with the image data in accordance with the reception status of the response signal from each of the plurality of shutter glasses 300 is just an example and is not necessarily limited to the aforementioned example. In a specific example, the display device 100 may switch the presentation mode of the image in accordance with the input image data from the mode related to the presentation of the three-dimensional image to the mode related to the presentation of the two-dimensional image in a case in which the display device recognizes that at least any of the plurality of shutter glasses 300 have not been able to properly receive the synchronization signal. In this case, the display device 100 switches the presentation mode of the image in accordance with the input image data to the mode related to the presentation of the two-dimensional image in any of the cases illustrated in FIGS. 8 and 9.

In addition, identification information may be applied to the plurality of shutter glasses 300, and the display device 100 may switch the display mode of the image in accordance with priorities associated with the identification information. The plurality of shutter glasses 300 stores the identification information with which each of the shutter glasses 300 can be identified. The display device 100 associates and stores the priorities of the respective shutter glasses 300 with the identification information. Specifically, a high priority is set for the shutter glasses 300 that are set as a monitoring target, and a low priority is set for the shutter glasses that are not set as the monitoring target. The display device 100 receives a response signal including the identification information of the shutter glasses 300 in response to the transmission of the synchronization signals to the shutter glasses 300. The display device 100 detects an ID of the shutter glasses 300 that fail to properly receive the synchronization signal on the basis of the reception status of the response signal from the shutter glasses 300. The display device 100 switches the presentation mode of the image in accordance with the priority associated with the detected ID. Here, the display device 100 switches the mode related to the presentation of the three-dimensional image to the mode related to the presentation of the two-dimensional image in a case in which the priority associated with the ID is high, and the display device 100 continues to present the three-dimensional image in a case in which the priority associated with the ID is low.

The example of operations related to the display of the image in accordance with the reception status of the responsive signal from each of the plurality of shutter glasses 300 in a case in which the display device 100 transmits the synchronization signals to the plurality of shutter glasses 300 have been described above as Modification Example 1 with reference to FIGS. 8 and 9.

(Modification Example 2: Switching on Shutter Glass Side)

Next, an example of a case in which a presentation mode of an image is selectively switched between a mode related to presentation of a three-dimensional image and a mode related to presentation of a two-dimensional image on the side of the shutter glass 300 will be described as Modification Example 2.

In the modification example, the presentation mode of the image is switched by controlling opening and closing timings of the left-eye shutter and the right-eye shutter on the side of the shutter glasses 300 even in a case in which the display device 100 displays the left-eye image and the right-eye image in the time division manner. Specifically, the shutter glasses 300 presents the two-dimensional image to the viewer by performing control such that the left-eye shutter and the right-eye shutter open or close at the same time in synchronization with a timing at which the display device 100 displays any of the left-eye image and the right-eye image.

Figure 10:
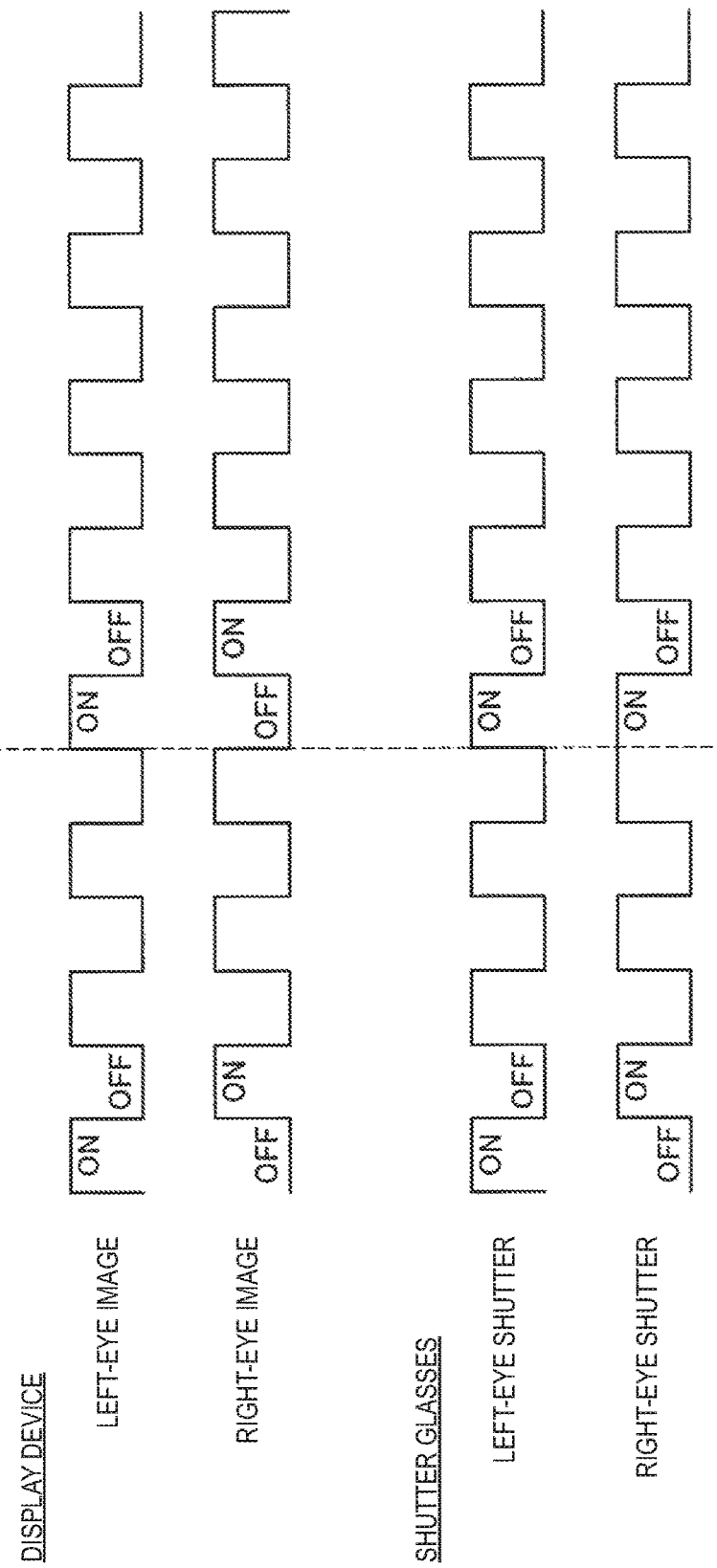
FIG. 10 is an explanatory diagram for explaining an outline of a medical information processing system according to Modification Example 2.

For example, FIG. 10 is an explanatory diagram for explaining an outline of a medical information processing system according to Modification Example 2 and illustrates an example of a timing chart related to presentation of an image by the medical information processing system. Specifically, the timing chart illustrated in FIG. 10 illustrates timings at which the display device 100 displays the left-eye image and the right-eye image and timings at which the shutter glasses 300 open and close each of the left-eye shutter and the right-eye shutter. Note that the ON state and the OFF state of the left-eye image and the right-eye image and the ON state and the OFF state of the left-eye shutter and the right-eye shutter in the example illustrated in FIG. 10 are similar to those in the example described with reference to FIG. 6.

In the example illustrated in FIG. 10, for example, the shutter glasses 300 switch the presentation of the three-dimensional image to the presentation of the two-dimensional image at the timing represented by the reference numeral t13. Specifically, at and before the timing t13, the shutter glasses 300 controls opening and closing of the left-eye shutter and the right-eye shutter in a similar manner to that in the example described with reference to FIG. 6. That is, the viewer observes the image that is a display target as a three-dimensional image at and before the timing t13.

Meanwhile, the shutter glasses 300 perform control such that both the left-eye shutter and the right-eye shutter are opened in synchronization with the timing at which the left-eye image is displayed at and after the timing t13. That is, the left-eye image is observed by both the left and right eyes of the viewer at the timing. In addition, the shutter glasses 300 perform control such that both the left-eye shutter and the right-eye shutter are closed in synchronization with the timing at which the right-image is displayed. That is, the image (that is, the right-eye image) is not observed by both the left and right eyes of the viewer at the timing. Under the control as described above, the viewer observes the image that is a display target as a two-dimensional image at and after the timing t13.

Note that trigger of the switching is not particularly limited as long as the shutter glasses 300 can perform the switching in accordance with a predetermined condition. In a specific example, the shutter glasses 300 may be provided with an input section such as a switch, and the shutter glasses 300 may switch the presentation mode of the image between the mode related to the presentation of the three-dimensional image and the mode related to the presentation of the two-dimensional image in response to an operation performed on the input section.

The example of the case in which the presentation mode of the image is selectively switched between the mode related to the presentation of the three-dimensional image and the mode related to the presentation of the two-dimensional image on the side of the shutter glasses 300 have been described above as Modification Example 2 with reference to FIG. 10.

<4. Application Examples>

Next, application examples of the medical information processing system according to an embodiment of the present disclosure will be described. The example of the case in which the medical stereoscopic observation device in the medical information processing system according to an embodiment of the present disclosure is applied to a surgical video microscope device has been described above. Meanwhile, the device applied as the medical stereoscopic observation device in the medical information processing system according to the embodiment is not necessarily limited only to the surgical video microscope device. Thus, an example of a device that can be applied as the medical stereoscopic observation device in the medical information processing system according to the embodiment will be described below.

<4.1. First Application Example: Hard Endoscope Device>

Figure 11:
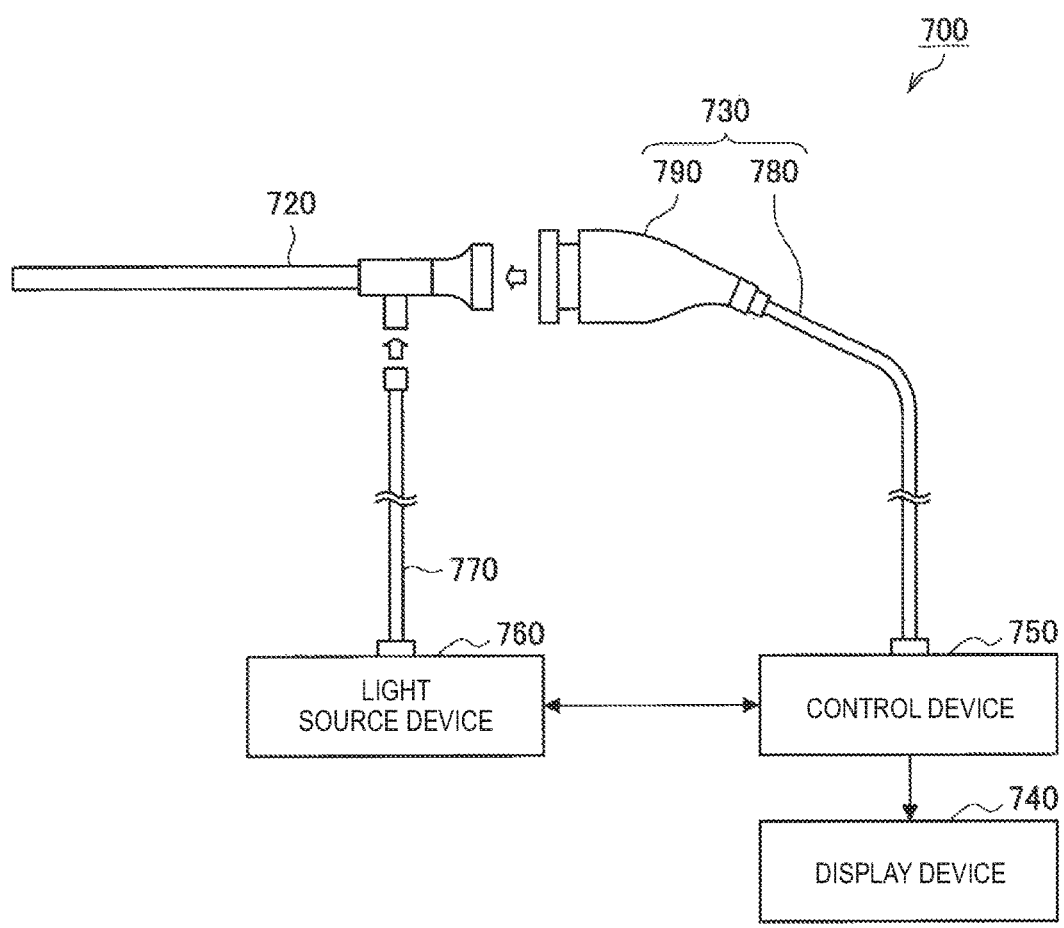
FIG. 11 is an explanatory diagram for explaining an example of a medical stereoscopic observation device that is applied to the medical information processing system according to the embodiment.
Figure 12:
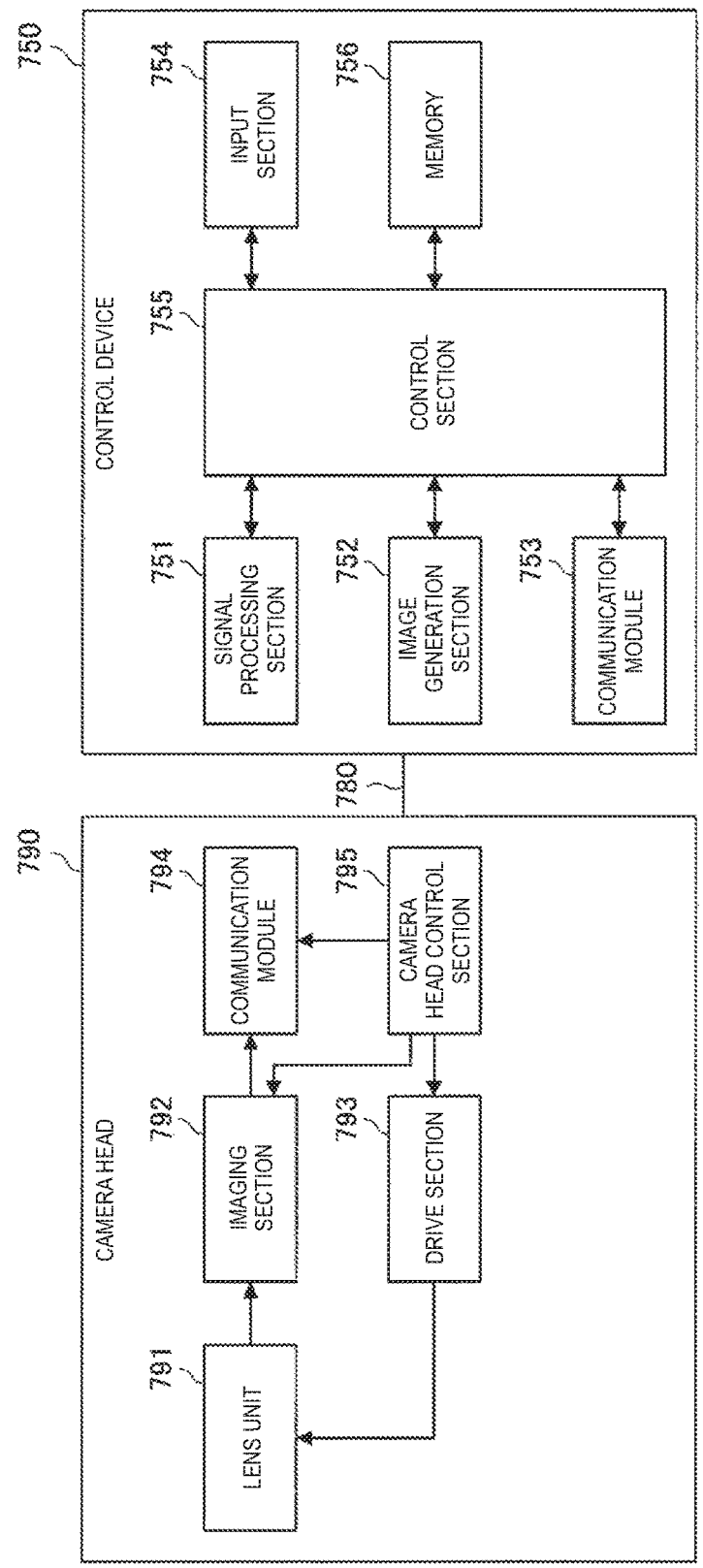
FIG. 12 is an explanatory diagram for explaining an example of a medical stereoscopic observation device that is applied to the medical information processing system according to the embodiment.

First, a first application example of the embodiment will be described with reference to FIGS. 11 and 12. In the application example, an example of a case in which a so-called hard endoscope device is applied as the medical stereoscopic observation device in the medical information processing system according to the embodiment will be described. For example, FIG. 11 is an explanatory diagram for explaining an example of the medical stereoscopic observation device that is applied to the medical information processing system according to the embodiment and illustrates an example of an outline configuration of a hard endoscope device. An endoscope device 700 is a device used in the medical field to observe an object inside an observation target such as a person (inside a living body). This endoscope device 700 includes an endoscope 720, an imaging device 730 (medical imaging device), a display device 740, a control device 750 (image processing device), and a light source device 760, and the imaging device 730 and the control device 750 configure a medical image acquisition system as illustrated in FIG. 11. Note that the endoscope 720 and the imaging device 730 configure an endoscope device using a hard mirror in the application example.

The light source device 760 has a light guide 770 with one end connected to the endoscope 720 and supplies while illumination light for illuminating the inside of the living body to the one end of the light guide 770. The light guide 770 has the one end that is detachably connected to the light source device 760 and the other end that is detachably connected to the endoscope 720. In addition, the light guide 770 delivers the light supplied by the light source device 760 from the one end to the other end and supplies the light to the endoscope 720.

The imaging device 730 captures an image of an object from the endoscope 720 and outputs the result of capturing the image. The imaging device 730 includes a transmission cable 780 that is a signal transmission section and a camera head 790 as illustrated in FIG. 11. In the embodiment 1, the transmission cable 780 and the camera head 790 form the medical imaging device.

The endoscope 720 is hard, has a thin and long shape, and is inserted into a living body. An optical system that includes one or a plurality of lenses and collects light of the object image is provided inside the endoscope 720. The endoscope 720 emits light supplied via the light guide 770 from a leading edge and irradiates the inside of the living body. Then, the light with which the inside of the living body is irradiated (object image) is collected by the optical system (lens unit 791) inside the endoscope 720.

The camera head 790 is detachably connected to a base end of the endoscope 720. In addition, the camera head 790 captures the object image, the light of which has been collected by the endoscope 720, under control of the control device 730 and outputs an imaging signal by the image capturing.

The transmission cable 780 has one end that is detachably connected to the control device 750 via a connector and the other end that is detachably connected to the camera head 790 via the connector. Specifically, the transmission cable 780 is a cable with a plurality of electric wirings (omitted in the drawing) disposed inside an outer cover that is the outermost layer. The plurality of electric wirings are electric wirings for respectively delivering the imaging signal output from the camera head 790, the control signal output from the control device 750, the synchronization signal, a clock, and electric power to the camera head 790.

The display device 740 displays an image generated by the control device 750 (that is, a medical image) under control of the control device 750. Although the display device 740 preferably has the display section with the size of 55 inches or greater in order to facilitate obtaining a sense of immersion during observation, the display device 740 is not limited thereto.

The control device 750 processes the imaging signal that is input from the camera head 790 via the transmission cable 780, outputs an image signal to the display device 740, and also comprehensively controls the operations of the camera head 790 and the display device 740. Note that a detailed configuration of the control device 750 will be described later.

Next, configurations of the imaging device 730 and the control device 750 will be described. FIG. 12 is an explanatory diagram for explaining an example of the medical stereoscopic observation device that is applied to the medical information processing system according to the embodiment and is a block diagram illustrating configurations of the imaging device 730 and the control device 750. Note that the illustration of the connector that enables attachment and detachment between the camera head 790 and the transmission cable 780 is omitted in FIG. 12.

Hereinafter, description will be given in the order of the configuration of the control device 750 and the configuration of the camera head 790. Note that main parts according to an embodiment of the present disclosure will be mainly described below as the configuration of the control device 750. The control device 750 includes a signal processing section 751, an image generation section 752, a communication module 753, an input section 754, a control section 755, and a memory 756 as illustrated in FIG. 12. Note that the control device 750 may be provided with a power supply section (omitted in the drawing) or the like that generates electric power voltage for driving the control device 750 and the camera head 790, supplies the electric power voltage to each part of the control device 750, and also supplies the electric power voltage to the camera head 790 via the transmission cable 780.

The signal processing section 751 outputs the imaging signal (pulse signal) digitalized by performing signal processing, such as noise removal or A/D conversion as necessary, on the imaging signal output from the camera head 790 to the image generation section 752.

In addition, the signal processing section 751 generates synchronization signals and clocks for the imaging device 730 and the control device 750. The synchronization signal (a synchronization signal or the like for providing an instruction for an imaging timing of the camera head 790, for example) and the clock (a clock for serial communication, for example) for the imaging device 730 are transmitted to the imaging device 730 via a line which is not illustrated in the drawing, and the imaging device 730 is driven on the basis of the synchronization signal and the clock.

The image generation section 752 generates an image signal for display that is to be displayed by the display device 740, on the basis of the imaging signal input from the signal processing section 751. The image generation section 752 executes predetermined signal processing on the imaging signal and generates the image signal for display that includes the object image. Here, various kinds of image processing such as interpolation processing, color correction processing, color emphasis processing, and outline emphasis processing are exemplified as the image processing. The image generation section 752 outputs the generated image signal to the display device 740.

The communication module 753 outputs the signal from the control device 750, which includes a control signal transmitted from the control section 755 as will be described later, to the imaging device 730. In addition, the communication module 753 outputs the signal from the imaging device 730 to the control device 750. That is, the communication module 753 is a relay device that collectively outputs signals from the respective parts of the control device 750, which are to be output to the imaging device 730, by parallel-serial conversion or the like, for example, and divides the signals input from the imaging device 730 by serial-parallel conversion or the like, for example, and outputs the signals to the respective parts of the control device 750.

The input section 754 is realized by a user interface such as a keyboard, a mouse, and a touch panel and receives inputs of various kinds of information.

The control section 755 performs drive control of the respective components including the control device 750 and the camera head 790, control of inputs and outputs of information to and from the respective components, and the like. The control section 755 generates a control signal with reference to communication information data (for example, communication format information and the like) that is recorded in the memory 756 and transmits the generated control signal to the imaging device 730 via the communication module 753. In addition, the control section 755 outputs the control signal to the camera head 790 via the transmission cable 780.

The memory 756 is realized by a semiconductor memory such as a flash memory or a dynamic random access memory (DRAM) and records communication information data (for example, communication format information and the like). Note that the memory 756 may record various programs and the like to be executed by the control section 755).

Note that the signal processing section 751 may have an AF processing section that outputs a predetermined AF evaluation value of each frame on the basis of an imaging signal of an input frame and an AF computation section that performs AF computation processing of selecting a frame, a focus lens position, or the like that is most suitable for the focal position from among AF evaluation values of the respective frames from the AF processing section.

Note that aforementioned signal processing section 751, the image generation section 752, the communication module 753, and the control section 755 are realized by a general-purpose processor such as a central processing unit (CPU) that has an internal memory (omitted in the drawing) that records programs or a dedicated processor such as various computation circuits that execute specific functions, such as an application specific integrated circuit (ASIC). In addition, the signal processing section 751, the image generation section 752, the communication module 753, and the control section 755 may be configured with a field programmable gate array (FPGA: omitted in the drawing) that is a type of programmable integrated circuits. Note that in a case in which the signal processing section 751, the image generation section 752, the communication module 753, and the control section 755 are configured with a FPGA, a memory that stores configuration data may be provided, and the FPGA that is a programmable integrated circuit may be configured by the configuration data read from the memory.

Next, main parts of the present disclosure will be mainly described as the configuration of the camera head 790. The camera head 790 includes a lens unit 791, an imaging section 792, a drive section 793, a communication module 794, and a camera head control section 795 as illustrated in FIG. 12.

The lens unit 791 includes one or a plurality of lenses and forms an object image, the light of which has been collected by the endoscope 720, on an imaging plane of an imaging element that forms the imaging section 792. The one or a plurality of lenses are configured to move along an optical axis. In addition, the lens unit 791 is provided with an optical zooming mechanism (omitted in the drawing) that moves the one or a plurality of lenses to change the angle of view and a focus mechanism that changes a focal point. Not that the lens unit 791 may be provided with a diaphragm mechanism or an optical filter (a filter that cuts infrared rays, for example) that is freely inserted and detached on the optical axis as well as the optical zooming mechanism or the focus mechanism The imaging section 792 captures an image of an object under control of the camera head control section 795. The imaging section 792 includes two imaging elements, such as charge coupled devices (CCDs) or a complementary metal oxide semiconductors (CMOSs), that receive the light of the object image formed by the lens unit 791 and converts the light into an electric signal and a prism that splits observed light and cause the split light to be incident on the two respective imaging elements. In a case of the CCDs, a signal processing section (omitted in the drawing) that performs signal processing (A/D conversion or the like) on an electric signal (analog signal) from the imaging elements and outputs an imaging signal, for example is mounted on a sensor chip or the like. In a case of the CMOSs, a signal processing section that performs signal processing (A/D conversion or the like) on an electric signal (analog) converted from light, for example, and outputs an imaging signal is included in the imaging elements. A configuration of the imaging section 792 will be described later.

The drive section 793 has a driver that causes the optical zooming mechanism and the focus mechanism to operate under control of the camera head control section 795 and changes an angle of view and a focal position of the lens unit 791.

The communication module 794 outputs a signal transmitted from the control device 750 to the respective parts in the camera head 790, such as the camera head control section 795. In addition, the communication module 794 converts information related to a current state of the camera head 790 or the like into a signal format in accordance with a transmission scheme determined in advance and outputs the converted signal to the control device 750 via the transmission cable 780. That is, the communication module 794 is a relay device that divides the signals input from the control device 750 and the transmission cable 780 by serial-parallel conversion or the like, for example, outputs the signals to the respective parts of the camera heads 790, and collectively outputs the signals from the respective parts of the camera head 790, which are to be output to the control device 750 and the transmission cable 780, by parallel-serial conversion or the like, for example.

The camera head control section 795 controls the overall operations of the camera head 790 in accordance with a drive signal input via the transmission cable 780, an instruction signal output from an operation section by a user's operation performed on the operation section, such as a switch, provided to expose to the outer surface of the camera head 790, and the like. In addition, the camera head control section 795 outputs information related to the current state of the camera head 790 to the control device 750 via the transmission cable 780.

Note that the aforementioned drive section 793, the communication module 794, and the camera head control section 795 are realized by a general-purpose processor such as a central processing unit (CPU) that has an internal memory (omitted in the drawing) that records programs or a dedicated processor such as various computation circuits that execute specific functions, such as an application specific integrated circuit (ASIC). In addition, the drive section 793, the communication module 794, and the camera head control section 795 may be configured with an FPGA that is a type of a programmable integrated circuit. Note that in a case in which the drive section 793, the communication module 794, and the camera head control section 795 are configured with a FPGA, a memory that stores configuration data may be provided, and the FPGA that is a programmable integrated circuit may be configured by the configuration data read from the memory.

Note that a signal processing section that performs signal processing on the imaging signal generated by the communication module 794 and the imaging section 794 may be included in the camera head 790 and the transmission cable 780. Also, an imaging clock for driving the imaging section 792 and a driving clock for driving the drive section 793 may be generated on the basis of a reference clock generated by an oscillator (omitted in the drawing) that is provided inside the camera head 790 and may be output to each of the imaging section 792 and the drive section 793. Alternatively, timing signals of various kinds of processing performed by the imaging section 792, the drive section 793, and the camera head control section 795 may be generated on the basis of the synchronization signal input from the control device 750 via the transmission cable and may be output to each of the imaging section 792, the drive section 793, and the camera head control section 795. In addition, the camera head control section 795 may be provided in the transmission cable 780 or the control device 750 instead of the camera head 790.

Note that the display device 740 can correspond to the display device 100 described above with reference to FIG. 3.

The example of the case in which the so-called hard endoscope device is applied as the medical stereoscopic observation device in the medical information processing system according to the embodiment has been described above with reference to FIGS. 11 and 12.

<4.2. Second Application Example: Soft Endoscope Device>

Figure 13:
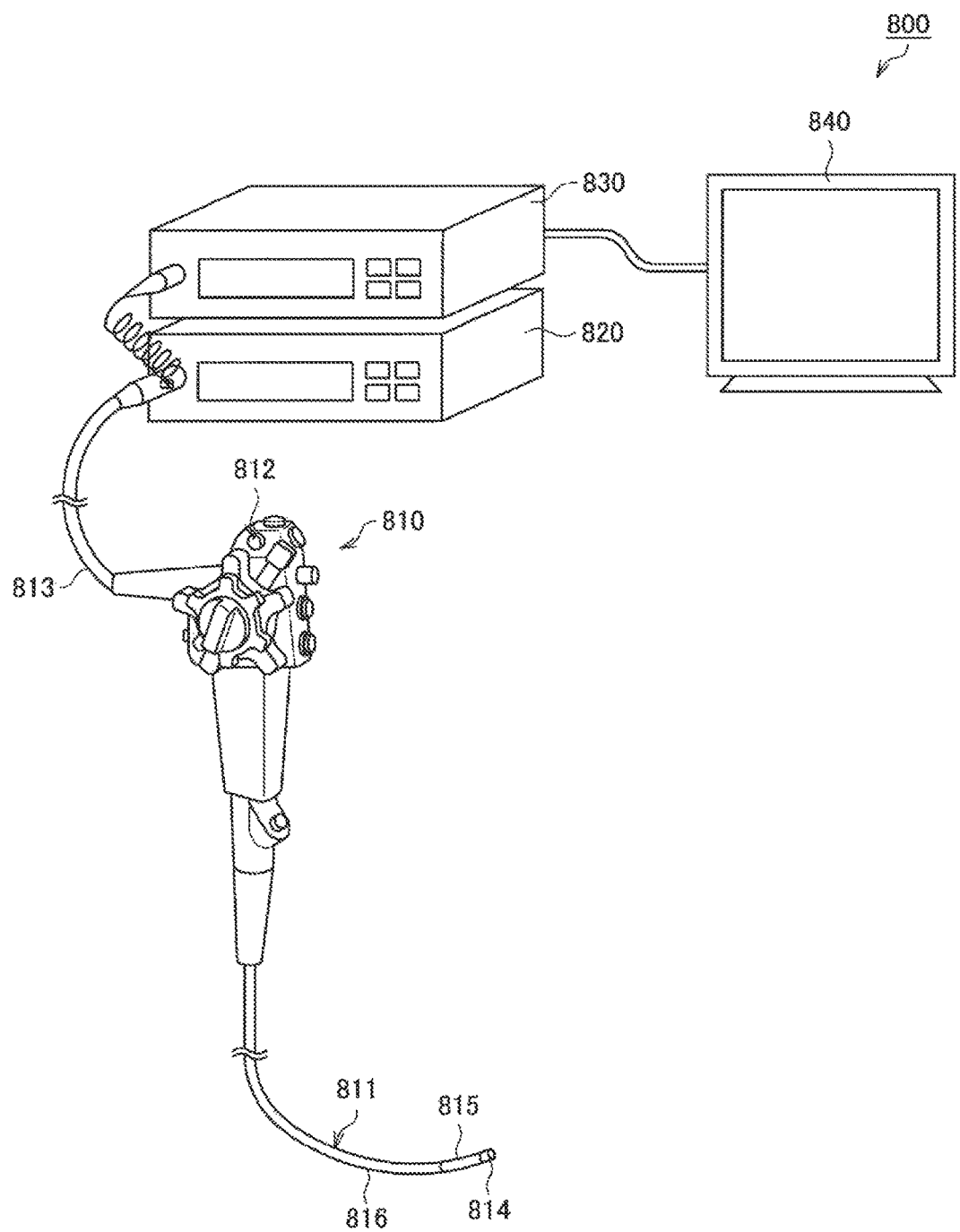
FIG. 13 is an explanatory diagram for explaining another example of a medical stereoscopic observation device that is applied to the medical information processing system according to the embodiment.

Next, a second application example of the embodiment will be described with reference to FIG. 13. In the application example, an example of a case in which a so-called soft endoscope device is applied as the medical stereoscopic observation device in the medical information processing system according to the embodiment will be described. FIG. 13 is an explanatory diagram for explaining another example of the medical stereoscopic observation device that is applied to the medical information processing system according to the embodiment and illustrates an example of an outline configuration of a soft endoscope device.

Although the endoscope device 700 using the hard mirror has been described as the endoscope 720 in the aforementioned first application example, the endoscope device 700 is not limited thereto, and an endoscope device using a soft mirror for the endoscope 720 may also be employed. In the second application example of the embodiment, an example of a case in which an imaging section is provided at a leading edge of an inserting section of the soft endoscope will be described.

An endoscope device 800 includes an endoscope 810 that inserts an inserting section 811 into a tested object, thereby imaging an image inside the body at an observation site and generating an electric signal, a light source device 820 that generates illumination light to be emitted from the leading edge of the endoscope 810, a control device 830 that performs predetermined image processing on the electric signal acquired by the endoscope 810 and comprehensively controls the overall operations of the endoscope device 800, and a display device 840 that displays the image inside the body, on which a processor section has performed image processing. The endoscope device 800 acquires the image inside the body of the tested object by inserting the inserting section 811 into the tested object such as a patient.

The endoscope 810 includes the inserting section 811 that has flexibility and a thin and long shape, an operation section 812 that is connected on the side of a base end of the inserting section 811 and receives inputs of various operation signals, and a universal code 813 that extends in a direction different from a direction in which the inserting section 811 extends from the operation section 812 and incorporates various cables that connect to the light source device 820 and the control device 830.

The inserting section 811 has a leading edge section 814 that incorporates the imaging section according to the application example, a bent section 815 that includes a plurality of bent pieces and is able to be freely bent, and a flexible tube section 816 that is connected on the side of a base end of the bent section 815 and has flexibility and a long shape.

Note that the display device 840 can correspond to the display device 100 described above with reference to FIG. 3, for example.

The example of the case in which the so-called soft endoscope device is applied as the medical stereoscopic observation device in the medical information processing system according to the embodiment has been described above with reference to FIG. 13.

Note that it is needless to say that the aforementioned first and second application examples are just application examples of the medical stereoscopic observation device according to the embodiment and are not intended to limit application targets of the medical stereoscopic observation device.

<5. Hardware Configuration>

Figure 14:
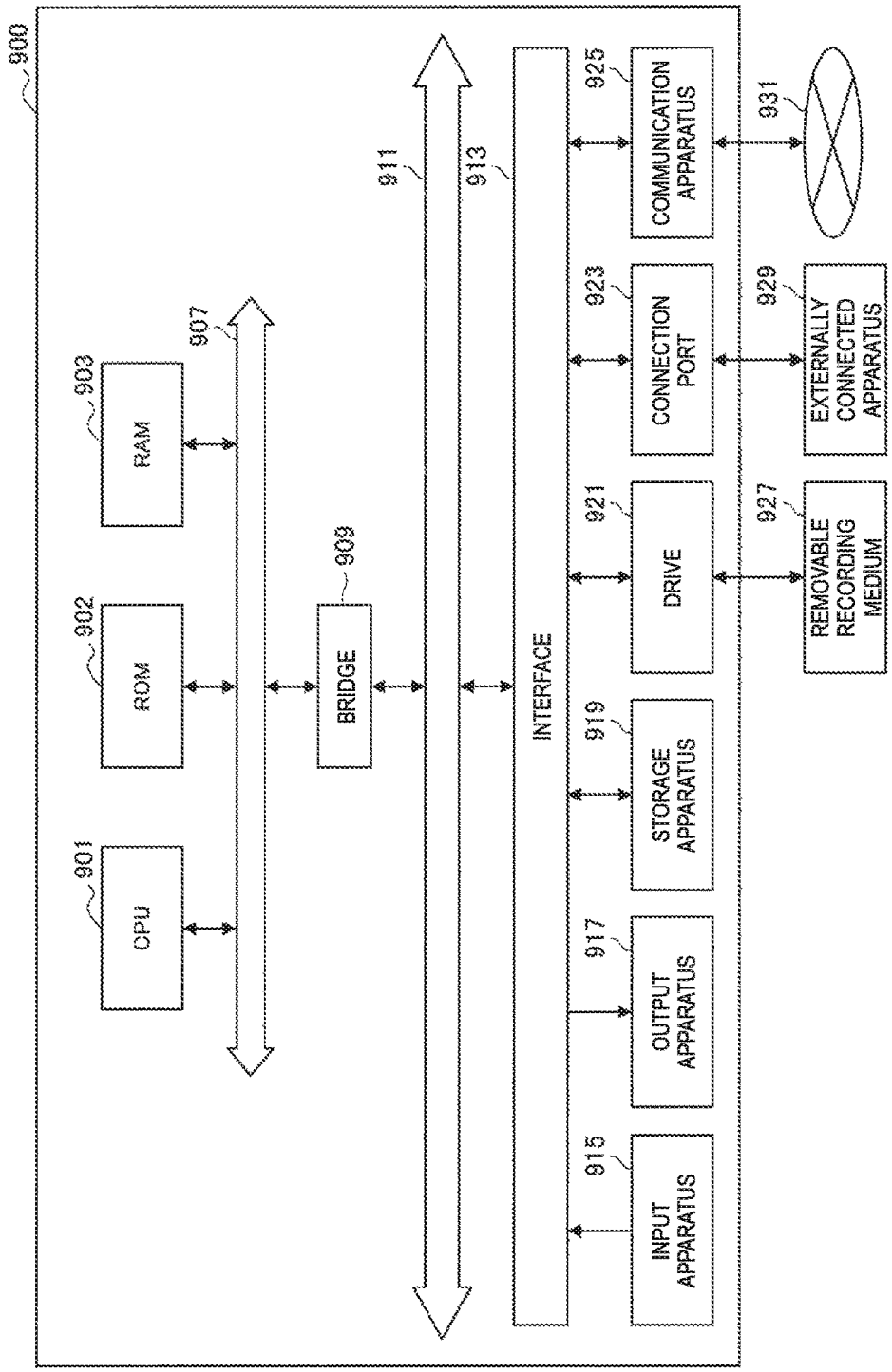
FIG. 14 is a functional block diagram illustrating a configuration example of a hardware configuration of an information processing apparatus that forms a medical information processing system according to an embodiment of the present disclosure.

Next, a hardware configuration of an information processing apparatus 900 that forms the medical information processing system according to the embodiment will be described in detail with reference to FIG. 14. FIG. 14 is a functional block diagram illustrating a configuration example of a hardware configuration of the information processing apparatus 900 that forms the medical information processing system according to an embodiment of the present disclosure.

The information processing apparatus 900 constituting a medical stereoscopic observation system according to the present embodiment is equipped primarily with a CPU 901, ROM 903, and RAM 905. Additionally, the information processing apparatus 900 may also be equipped with a host bus 907, a bridge 909, an external bus 911, an interface 913, an input apparatus 915, an output apparatus 917, a storage apparatus 919, a drive 921, a connection port 923, and a communication apparatus 925.

The CPU 901 serves as an arithmetic processing apparatus and a control apparatus, and controls the overall operation or a part of the operation of the information processing apparatus 900 according to various programs recorded in the ROM 903, the RAM 905, the storage apparatus 919, or a removable recording medium 927. The ROM 903 stores programs, operation parameters, and the like used by the CPU 901. The RAM 905 primarily stores programs that the CPU 901 uses and parameters and the like varying as appropriate during the execution of the programs. These are connected with each other via the host bus 907 configured from an internal bus such as a CPU bus or the like. Note that the display control section 103 and the synchronization control section 105 described earlier with reference to FIG. 4 may be realized by the CPU 901, for example.

The host bus 907 is connected to the external bus 911 such as a PCI (Peripheral Component Interconnect/Interface) bus via the bridge 909. Additionally, the input apparatus 915, the output apparatus 917, the storage apparatus 919, the drive 921, the connection port 923, and the communication apparatus 925 are connected to the external bus 911 via the interface 913.

The input apparatus 915 is an operation mechanism operated by a user, such as a mouse, a keyboard, a touch panel, buttons, a switch, a lever, or a pedal. Also, the input apparatus 915 may be a remote control mechanism (a so-called remote control) using, for example, infrared light or other radio waves, or may be an externally connected apparatus 929 such as a mobile phone or a PDA conforming to the operation of the information processing apparatus 900. Furthermore, the input apparatus 915 generates an input signal based on, for example, information which is input by a user with the above operation mechanism, and is configured from an input control circuit for outputting the input signal to the CPU 901. The user of the information processing apparatus 900 can input various data to the information processing apparatus 900 and can instruct the information processing apparatus 900 to perform processing by operating this input apparatus 915.

The output apparatus 917 is configured from a device capable of visually or audibly notifying acquired information to a user. Examples of such device include display apparatuses such as a CRT display apparatus, a liquid crystal display apparatus, a plasma display apparatus, an EL display apparatus and lamps, audio output apparatuses such as a speaker and a headphone, a printer, and the like. For example, the output apparatus 917 outputs a result obtained by various processing performed by the information processing apparatus 900. More specifically, the display apparatus displays, in the form of texts or images, a result obtained by various processes performed by the information processing apparatus 900. On the other hand, the audio output apparatus converts an audio signal such as reproduced audio data and sound data into an analog signal, and outputs the analog signal. For example, the display section 101 described earlier with reference to FIG. 4 may be realized by the output apparatus 917.

The storage apparatus 919 is a device for storing data configured as an example of a storage unit of the information processing apparatus 900 and is used to store data. The storage apparatus 919 is configured from, for example, a magnetic storage apparatus such as a HDD (Hard Disk Drive), a semiconductor storage apparatus, an optical storage apparatus, or a magneto-optical storage apparatus. This storage apparatus 919 stores programs to be executed by the CPU 901, and various data.

The drive 921 is a reader/writer for recording medium, and is embedded in the information processing apparatus 900 or attached externally thereto. The drive 921 reads information recorded in the attached removable recording medium 927 such as a magnetic disk, an optical disk, a magneto-optical disk, or a semiconductor memory, and outputs the read information to the RAM 905. Furthermore, the drive 921 can write in the attached removable recording medium 927 such as a magnetic disk, an optical disk, a magneto-optical disk, or a semiconductor memory. The removable recording medium 927 is, for example, a DVD medium, an HD-DVD medium, or a Blu-ray (a registered trademark) medium. The removable recording medium 927 may be a CompactFlash (CF; a registered trademark), a flash memory, an SD memory card (Secure Digital Memory Card), or the like. Alternatively, the removable recording medium 927 may be, for example, an IC card (Integrated Circuit Card) equipped with a non-contact IC chip or an electronic appliance.

The connection port 923 is a port for allowing apparatuses to directly connect to the information processing apparatus 900. Examples of the connection port 923 include a USB (Universal Serial Bus) port, an IEEE1394 port, a SCSI (Small Computer System Interface) port, and the like. Other examples of the connection port 923 include an RS-232C port, an optical audio terminal, an HDMI (a registered trademark) (High-Definition Multimedia Interface) port, and the like. By the externally connected apparatus 929 connecting to this connection port 923, the information processing apparatus 900 directly obtains various data from the externally connected apparatus 929 and provides various data to the externally connected apparatus 929. For example, the image input section 102 described above with reference to FIG. 4 can be realized by the connection port 923.

The communication apparatus 925 is a communication interface configured from, for example, a communication apparatus for connecting to a communication network 931. The communication apparatus 925 is, for example, a wired or wireless LAN (Local Area Network), Bluetooth (registered trademark), a communication card for WUSB (Wireless USB), or the like. Alternatively, the communication apparatus 925 may be a router for optical communication, a router for ADSL (Asymmetric Digital Subscriber Line), a modem for various communications, or the like. This communication apparatus 925 can transmit and receive signals and the like in accordance with a predetermined protocol such as TCP/IP on the Internet and with other communication apparatuses, for example. The communication network 931 connected to the communication apparatus 925 is configured from a network and the like, which is connected via wire or wirelessly, and may be, for example, the Internet, a home LAN, infrared communication, radio wave communication, satellite communication, or the like. For example, the communication section 107 described with reference to FIG. 4 can be realized by the communication apparatus 925.

Heretofore, an example of the hardware configuration capable of realizing the functions of the information processing apparatus 900 constituting a medical information processing system according to the embodiment of the present disclosure has been shown. Each of the structural elements described above may be configured using a general-purpose material, or may be configured from hardware dedicated to the function of each structural element. Accordingly, the hardware configuration to be used can be changed as appropriate according to the technical level at the time of carrying out the present embodiment. Note that, although not illustrated in FIG. 14, the various structural elements corresponding to the information processing apparatus 900 constituting a medical information processing system (in other words, a surgical video microscope device or an image processing device) obviously are provided.

Note that it is also possible to develop a computer program for realizing the respective functions of the information processing apparatus 900 constituting a medical information processing system according to the present embodiment as described above, and implement the computer program in a personal computer or the like. In addition, a computer-readable recording medium storing such a computer program may also be provided. The recording medium may be a magnetic disc, an optical disc, a magneto-optical disc, or flash memory, for example. Furthermore, the above computer program may also be delivered via a network, for example, without using a recording medium. In addition, the number of computers that causes the computer program to be executed is not particularly limited. For example, a plurality of computers (for example, a plurality of servers and the like) may cooperate with each other and execute the computer program.

<6. Conclusion>

As described above, a three-dimensional image is presented to a viewer on the basis of the shutter glasses scheme in the medical information processing system according to the embodiment. That is, the display device 100 performs control such that a left-eye image and a right-eye image are displayed on a predetermined display section in the time division manner. In addition, the display device 100 transmits synchronization signals in accordance with the display timings of the left-eye image and the right-eye image to the shutter glasses 300 and receives a response to the synchronization signal from the shutter glasses 300. Then, the display device 100 performs control such that only any one of the left-eye image and the right-eye image is displayed on the display section in accordance with the reception status of the response, thereby allowing the viewer to observe a two-dimensional image.

With the configuration as described above, the display device 100 can switch the presentation mode of the image (for example, a medical image) in accordance with input image data to the mode related to the presentation of the two-dimensional image in a case in which it becomes difficult to establish synchronization with the shutter glasses 300 (that is, in a case in which it becomes difficult to observe the three-dimensional image). In this manner, even in a case in which it becomes difficult to observe the three-dimensional image, it is possible to maintain the state in which observation of a target displayed as an image (in other words, observation of an image of a display target) is available (that is, to allow the viewer to continue the observation) while it is difficult to observe an image that leads to a sense of perspective.

It should be understood by those skilled in the art that various modifications, combinations, sub-combinations and alterations may occur depending on design requirements and other factors insofar as they are within the scope of the appended claims or the equivalents thereof.

Further, the effects described in this specification are merely illustrative or exemplified effects, and are not limitative. That is, with or in the place of the above effects, the technology according to an embodiment of the present disclosure may achieve other effects that are clear to those skilled in the art from the description of this specification.

Additionally, the present technology may also be configured as below.

(1) A medical image display apparatus including:
a display control section that performs control such that a left-eye image and a right-eye image that form a medical image are displayed in a time division manner on a predetermined display section; and
a communication section that transmits a synchronization signal in accordance with display timings of the left-eye image and the right-eye image on the display section to shutter glasses that include a left-eye shutter and a right-eye shutter, and receives a response to the synchronization signal from the shutter glasses,
in which the display control section performs the control such that only any one of the left-eye image and the right-eye image is displayed on the display section in accordance with a reception status of the response.

(2) The medical image display apparatus according to (1), in which the display control section performs the control such that only any one of the left-eye image and the right-eye image is displayed on the display section in a case in which the response has not been properly received.

(3) The medical image display apparatus according to (1) or (2),
in which the communication section transmits the synchronization signal to each of the plurality of shutter glasses and receives the response to the synchronization signal from each of the plurality of shutter glasses, and
the display control section performs the control such that only any one of the left-eye image and the right-eye image is displayed on the display section in accordance with the reception status of the response from each of the plurality of shutter glasses.

(4) The medical image display apparatus according to (3), in which the display control section performs the control such that only any one of the left-eye image and the right-eye image is displayed on the display section in a case in which the response has not been properly received from the shutter glasses that have been set as a monitoring target from among the plurality of shutter glasses.

(5) The medical image display apparatus according to (4), in which the display control section performs the control such that time-division display of the left-eye image and the right-eye image is continued in a case in which the response has not been properly received from the shutter glasses that have not been set as a monitoring target from among the plurality of shutter glasses.

(6) The medical image display apparatus according to (3), in which the display control section performs the control such that only any one of the left-eye image and the right-eye image is displayed on the display section in a case in which the response has not been received from at least part of the plurality of shutter glasses.

(7) The medical image display apparatus according to any one of (1) to (6), including:
the display section.

(8) A medical information processing system including:
a medical image display apparatus that controls display of a medical image on a predetermined display section; and
shutter glasses that include a left-eye shutter and a right-eye shutter,
in which the medical image display apparatus includes
a display control section that performs the control such that a left-eye image and a right-eye image that form the medical image are displayed in a time division manner on the display section, and a communication section that transmits a synchronization signal in accordance with display timings of the left-eye image and the right-eye image on the display section to the shutter glasses, and receives a response to the synchronization signal from the shutter glasses, the shutter glasses include a shutter control section that controls closing and opening of each of the left-eye shutter and the right-eye shutter on a basis of the synchronization signal, and the display control section performs the control such that only any one of the left-eye image and the right-eye image is displayed on the display section in accordance with a reception status of the response.

(9) The medical information processing system according to (8), in which the shutter control section performs the control such that both the left-eye shutter and the right-eye shutter open and close in synchronization with a display timing of any one of the left-eye image and the right-eye image in accordance with a predetermined condition.

(10) The medical information processing system according to (9), in which the shutter control section performs the control such that both the left-eye shutter and the right-eye shutter open and close in synchronization with the display timing of any one of the left-eye image and the right-eye image in accordance with a user's input via a predetermined input section.

(11) The medical information processing system according to any one of (8) to (10), including:

a medical imaging unit that captures an image of an affected site by a predetermined imaging section, in which the display control section causes the display section to display a left-eye image and a right-eye image in accordance with a result of capturing the affected site by the imaging section in a time division manner.

(12) A medical image display control method including, by a computer:

performing control such that a left-eye image and a right-eye image that form a medical image are displayed in a time division manner on a predetermined display section;

transmitting a synchronization signal in accordance with display timings of the left-eye image and the right-eye image on the display section to shutter glasses that include a left-eye shutter and a right-eye shutter, and receiving a response to the synchronization signal from the shutter glasses; and performing control such that only any one of the left-eye image and the right-eye image is displayed on the display section in accordance with a reception status of the response.

What is claimed is:

1. A medical image display controlling apparatus comprising:

processing circuitry configured to:

control such that a left-eye image and a right-eye image that form a medical image are displayed in a time division manner on a predetermined display, transmit a synchronization signal to each of the plurality of shutter glasses in accordance with display timings of the left-eye image and the right-eye image on the display to shutter glasses that include a left-eye shutter and a right-eye shutter, and receive a response to the synchronization signal from each of the plurality of shutter glasses, wherein the processing circuitry is further configured to control such that only one of the left-eye image and the right-eye image is displayed on the display in a case in which the response has not been received from the shutter glasses that have been set as a monitoring target from among the plurality of shutter glasses.

2. The medical image display controlling apparatus according to claim 1, wherein the processing circuitry controls such that only one of the left-eye image and the right-eye image is displayed on the display in a case in which the response has not been received.

3. The medical image display controlling apparatus according to claim 1, wherein the processing circuitry controls such that time-division display of the left-eye image and the right-eye image is continued in a case in which the response has not been received from the shutter glasses that have not been set as a monitoring target from among the plurality of shutter glasses.

4. The medical image display controlling apparatus according to claim 1, wherein the processing circuitry controls such that only one of the left-eye image and the right-eye image is displayed on the display in a case in which the response has not been received from at least part of the plurality of shutter glasses.

5. The medical image display controlling apparatus according to claim 1, comprising:

a display device, wherein the predetermined display is the display device of the medical image display controlling apparatus.

6. A medical information processing system comprising:

a medical image display apparatus including first processing circuitry configured to control display of a medical image on a predetermined display; and a plurality of shutter glasses that each include a left-eye shutter and a right-eye shutter, wherein the first processing circuitry of the medical image display apparatus is further configured to control such that a left-eye image and a right-eye image that form the medical image are displayed in a time division manner on the display, and transmit a synchronization signal in accordance with display timings of the left-eye image and the right-eye image on the display to the plurality of shutter glasses, and receive a response to the synchronization signal from the plurality of shutter glasses, wherein each of the shutter glasses includes second processing circuitry configured to control closing and opening of each of the left-eye shutter and the right-eye shutter on a basis of the synchronization signal, and control such that only one of the left-eye image and the right-eye image is displayed on the display in accordance with a reception status of the response, wherein the first processing circuitry is further configured to control such that only one of the left-eye image and the right-eye image is displayed on the display in a case in which the response has not been received from shutter glasses that have been set as a monitoring target from among the plurality of shutter glasses.

7. The medical information processing system according to claim 6, wherein the second processing circuitry is further configured to control such that both the left-eye shutter and the right-eye shutter open and close in synchronization with a display timing of one of the left-eye image and the right-eye image in accordance with a predetermined condition.

8. The medical information processing system according to claim 7, wherein the second processing circuity is further configured to control such that both the left-eye shutter and the right-eye shutter open and close in synchronization with the display timing of one of the left-eye image and the right-eye image in accordance with a user's input via a predetermined input.

9. The medical information processing system according to claim 6, comprising:
a medical imaging device that captures an image of an affected site by a predetermined camera,
wherein the first processing circuitry is further configured to control the display to display the left-eye image and the right-eye image in accordance with a result of capturing the affected site by the camera in the time division manner.

10. A medical image display control method comprising, by a computer:
controlling such that a left-eye image and a right-eye image that form a medical image are displayed in a time division manner on a predetermined display;
transmitting a synchronization signal in accordance with display timings of the left-eye image and the right-eye image on the display to a plurality of shutter glasses that include a left-eye shutter and a right-eye shutter, and receiving a response to the synchronization signal from the plurality of shutter glasses;
controlling such that only one of the left-eye image and the right-eye image is displayed on the display in accordance with reception status of the response; and
controlling such that only one of the left-eye image and the right-eye image is displayed on the display in a case in which the response has not been received from the shutter glasses that have been set as a monitoring target from among the plurality of shutter glasses.

* * * * *